US009863916B2

United States Patent
Tanaka et al.

(10) Patent No.: US 9,863,916 B2
(45) Date of Patent: *Jan. 9, 2018

(54) SENSOR APPARATUS

(71) Applicant: Kyocera Corporation, Kyoto (JP)

(72) Inventors: Hiroyasu Tanaka, Kyoto (JP); Yasutaka Ohashi, Kyoto (JP)

(73) Assignee: KYOCERA CORPORATION, Kyoto (JP)

(*) Notice: Subject to any disclaimer, the term of this patent is extended or adjusted under 35 U.S.C. 154(b) by 172 days.

This patent is subject to a terminal disclaimer.

(21) Appl. No.: 14/764,073

(22) PCT Filed: Oct. 31, 2013

(86) PCT No.: PCT/JP2013/079592
§ 371 (c)(1),
(2) Date: Jul. 28, 2015

(87) PCT Pub. No.: WO2014/119069
PCT Pub. Date: Aug. 7, 2014

(65) Prior Publication Data
US 2015/0362464 A1 Dec. 17, 2015

(30) Foreign Application Priority Data
Jan. 30, 2013 (JP) .................. 2013-016248

(51) Int. Cl.
G01N 29/22 (2006.01)
G01N 29/02 (2006.01)

(52) U.S. Cl.
CPC ......... G01N 29/022 (2013.01); G01N 29/222 (2013.01); G01N 2291/0423 (2013.01)

(58) Field of Classification Search
CPC ................. G01N 29/022; G01N 2291/0423
(Continued)

(56) References Cited

U.S. PATENT DOCUMENTS 5,130,257 A 7/1992 Baer et al.
5,283,037 A 2/1994 Baer et al.
(Continued)

FOREIGN PATENT DOCUMENTS

JP 5-240762 A 9/1993
JP 2004-151016 A 5/2004
(Continued)

OTHER PUBLICATIONS

International Search Report dated Jan. 21, 2014 in International Application No. PCT/JP2013/079592, in 2 pages.

Primary Examiner — J M Saint Surin
(74) Attorney, Agent, or Firm — Duane Morris LLP

(57) ABSTRACT

A sensor apparatus includes a first cover member; a detection element including an element substrate located on the first cover member, and a detection portion configured to detect an analyte, the detection portion being located on the element substrate; a terminal located on the first cover member and electrically connected to the detection element; an intermediate cover member located on the first cover member and having a space with the detection element; a filler member located in the space between the detection element and the intermediate cover member; a second cover member configured to cover at least a part of the detection element and joined to at least one of the first cover member and the intermediate cover member; an inlet into which the analyte flows; and a flow passage which is continuous with the inlet, and extends at least to the detection portion.

16 Claims, 23 Drawing Sheets

(58) Field of Classification Search
USPC .......................................................... 73/649
See application file for complete search history.

(56) References Cited

U.S. PATENT DOCUMENTS

| | | | |
|---|---|---|---|
| 5,306,644 | A | 4/1994 | Myerholtz et al. |
| 6,235,488 | B1 | 5/2001 | Tom-Moy et al. |
| 2002/0192718 | A1 | 12/2002 | Tom-Moy et al. |
| 2005/0239194 | A1 | 10/2005 | Takahashi et al. |
| 2006/0049047 | A1 | 3/2006 | Sato |
| 2007/0284966 | A1* | 12/2007 | Kadota ................ G01N 29/022 |
| | | | 310/313 R |
| 2009/0115004 | A1 | 5/2009 | Carter et al. |
| 2016/0290967 | A1* | 10/2016 | Tanaka ................ G01N 29/022 |

FOREIGN PATENT DOCUMENTS

| | | |
|---|---|---|
| JP | 2005-249491 A | 9/2005 |
| JP | 2006-184011 A | 7/2006 |
| JP | 2007-520698 A | 7/2007 |
| JP | 2010-239477 A | 10/2010 |

\* cited by examiner (a)

(b)

(c)

(a)

(b)

(a)

(b)

SENSOR APPARATUS

RELATED APPLICATIONS

This application is a 35 U.S.C. §371 U.S. National Phase Application of PCT/JP2013/079592, which was filed on Oct. 31, 2013, which claims priority to Japanese Patent Application No. 2013-016248 filed on Jan. 30, 2013. The disclosures of these applications are incorporated herein by reference in their entireties

TECHNICAL FIELD

The present invention relates to a sensor apparatus capable of measuring properties of an analyte or ingredients contained in an analyte.

BACKGROUND ART

There has been known a sensor apparatus that measures properties of a liquid which is an analyte, or ingredients of a liquid, using a detection element such as a surface acoustic wave element (refer to Patent Literatures 1 to 3, for example).

For example, a sensor apparatus incorporating a surface acoustic wave element, which is constructed by disposing, on a piezoelectric substrate, a detection portion which reacts with a component contained in an analyte sample, is designed to detect properties or ingredients of a liquid which is an analyte by measuring variations in surface acoustic waves propagating through the detection portion. Such a measurement method using a surface acoustic wave element or the like has the advantage over other measurement methods (for example, enzyme method) in that it is adapted for a plurality of detection systems.

However, each conventional sensor apparatus incorporating a detection element such as a surface acoustic wave element in itself is devoid of a mechanism capable of fluid suction. Thus, to allow an analyte to flow into the detection portion, a procedural step of sucking the analyte using an instrument such as a micro pipette, and delivering the sucked analyte into the detection portion is required. This leads to an increase in the complexity of measurement operation. Furthermore, the placement of extra instruments as required results in scale-up of the measurement apparatus as a whole.

There is also known a sensor apparatus which adopts a different detection method from the detection method using a detection element such as a surface acoustic wave element. In this construction, a reagent containing, for example, an enzyme is applied in advance to a measuring electrode, and an analyte is caused to react with the applied reagent for the reading of changes in electric current in the measuring electrode (refer to Patent Literature 4).

In Patent Literature 4, there is disclosed a technique that enables the sensor apparatus in itself to effect suction of an analyte by exploiting capillary phenomenon. According to this technique, a narrow elongate analyte supply path is led out to the reagent-bearing part of the measuring electrode to wick an analyte so that it can be directed to the reagent-bearing part under capillary phenomenon.

Inconveniently, the analyte measurement method as disclosed in Patent Literature 4 that involves application of a reagent containing an enzyme or the like to the measuring electrode does not lend itself to examination on a plurality of items because of limitations upon the number of measurable examination items.

In the sensor apparatus described in Patent Literature 4, its measuring section is formed by applying a reagent to an electrode, wherefore the thickness of the measuring section is equivalent to the thickness of the electrode, that is; the measuring section is very thin. This allows the narrow analyte supply path to be elongated without discontinuity to the measuring section.

On the other hand, in the sensor apparatus incorporating a detection element such as a surface acoustic wave element, the detection element is constructed of, for example, a piezoelectric substrate, and thus has a certain thickness. In this case, even if the technology disclosed in Patent Literature 4 is applied, the analyte supply path may be obstructed by the detection element, thus making it difficult to pass an analyte to the detection portion.

CITATION LIST

Patent Literature 1: Japanese Unexamined Patent Publication JP-A 5-240762 (1993)
Patent Literature 2: Japanese Unexamined Patent Publication JP-A 2006-184011
Patent Literature 3: Japanese Unexamined Patent Publication JP-A 2010-239477
Patent Literature 4: Japanese Unexamined Patent Publication JP-A 2005-249491

SUMMARY OF INVENTION

Technical Problem

There has thus been sought after a sensor apparatus which incorporates a detection element such as a surface acoustic wave element having a certain thickness, and yet has a suction mechanism.

Solution to Problem

A sensor apparatus in accordance with an embodiment of the invention includes: a first cover member; a detection element including an element substrate located on an upper surface of the first cover member, and a detection portion configured to detect an analyte, the detection portion being located on an upper surface of the element substrate; a terminal located on the upper surface of the first cover member and electrically connected to the detection element; an intermediate cover member located on the upper surface of the first cover member and having a space with the detection element; a filler member located in the space between the detection element and the intermediate cover member; a second cover member configured to cover at least a part of the detection element and joined to at least one of the first cover member and the intermediate cover member; an inlet into which the analyte flows; and a flow passage which is continuous with the inlet, is surrounded by the intermediate cover member and the second cover member, and extends at least to the detection portion.

According to the sensor apparatus, since the detection element and the intermediate cover member which constitutes at least a part of the flow passage are juxtaposed on the upper surface of the first cover member, this makes it possible to attain an analyte flow passage extending from the inlet to the detection portion even with the use of a detection element having a certain thickness, and thereby deliver an analyte, which has been wicked through the inlet by, for example, capillary phenomenon to the detection portion. That is, the sensor apparatus incorporates a detection element having a certain thickness and yet includes, in itself, an analyte suction mechanism, and thus allows easy measurement operation. Moreover, the placement of the filler member between the detection element and the intermediate cover member in the space helps suppress interference of the space with capillary phenomenon, thus permitting smooth wicking of an analyte toward the detection element.

Moreover, a sensor apparatus in accordance with an embodiment of the invention includes: a first cover member having an element storage recess in an upper surface thereof; a detection element including an element substrate stored in the element storage recess, and at least one detection portion configured to detect an analyte, the detection portion being located on an upper surface of the element substrate; and a second cover member configured to cover the detection element and joined to the first cover member, the second cover member having an inlet into which an analyte flows and a groove extending from the inlet to at least a location above the detection portion.

A sensor apparatus in accordance with an embodiment of the invention comprises: a mounting member having, at an end thereof, an inlet into which an analyte flows, and also having, in an upper surface thereof, a groove which is continuous with the inlet; a detection element having at least one detection portion configured to detect an analyte at a main surface thereof, the detection element being mounted in the mounting member so that, with the main surface opposed to the upper surface of the mounting member, the detection portion is located above the groove; and a cover member having an element storage recess in a lower surface thereof, the cover member being joined to the mounting member so that the detection element can be stored in the element storage recess.

A sensor apparatus in accordance with an embodiment of the invention includes: a cover member having an inlet into which an analyte enters, a groove-shaped flow passage communicated with the inlet, and a concavely-curved cavity communicated with the flow passage; an element substrate stored in the cavity; and a detection element located on an upper surface of the element substrate, the detection element having a detection portion which reacts with a component contained in the analyte.

According to the sensor apparatus mentioned above, the detection element is stored in the element storage recess of the first cover member. This makes it possible to attain an analyte flow passage extending from the inlet to the detection portion even with the use of a detection element having a certain thickness, and thereby deliver an analyte, which has been wicked through the inlet by, for example, capillary phenomenon to the detection portion. That is, there is provided a sensor apparatus which incorporates a detection element having a certain thickness and yet includes, in itself, an analyte suction mechanism, and thus allows easy measurement operation.

DESCRIPTION OF EMBODIMENTS

Hereinafter, embodiments of a sensor apparatus pursuant to the invention will be described in detail with reference to drawings. In each drawing to be referred to in the following description, like constituent members are identified with the same reference symbols. Moreover, for example, the size of each member and the distance between the individual members are schematically shown in each drawing and may therefore be different from the actual measurements.

Moreover, although each side of the sensor apparatus may be either an upper side or a lower side, in the following description, for purposes of convenience, an x-y-z rectangular coordinate system is defined, and thus terms such as an upper surface and a lower surface are used on the understanding that a positive z direction corresponds to an upward direction.

First Embodiment

Figure 2:
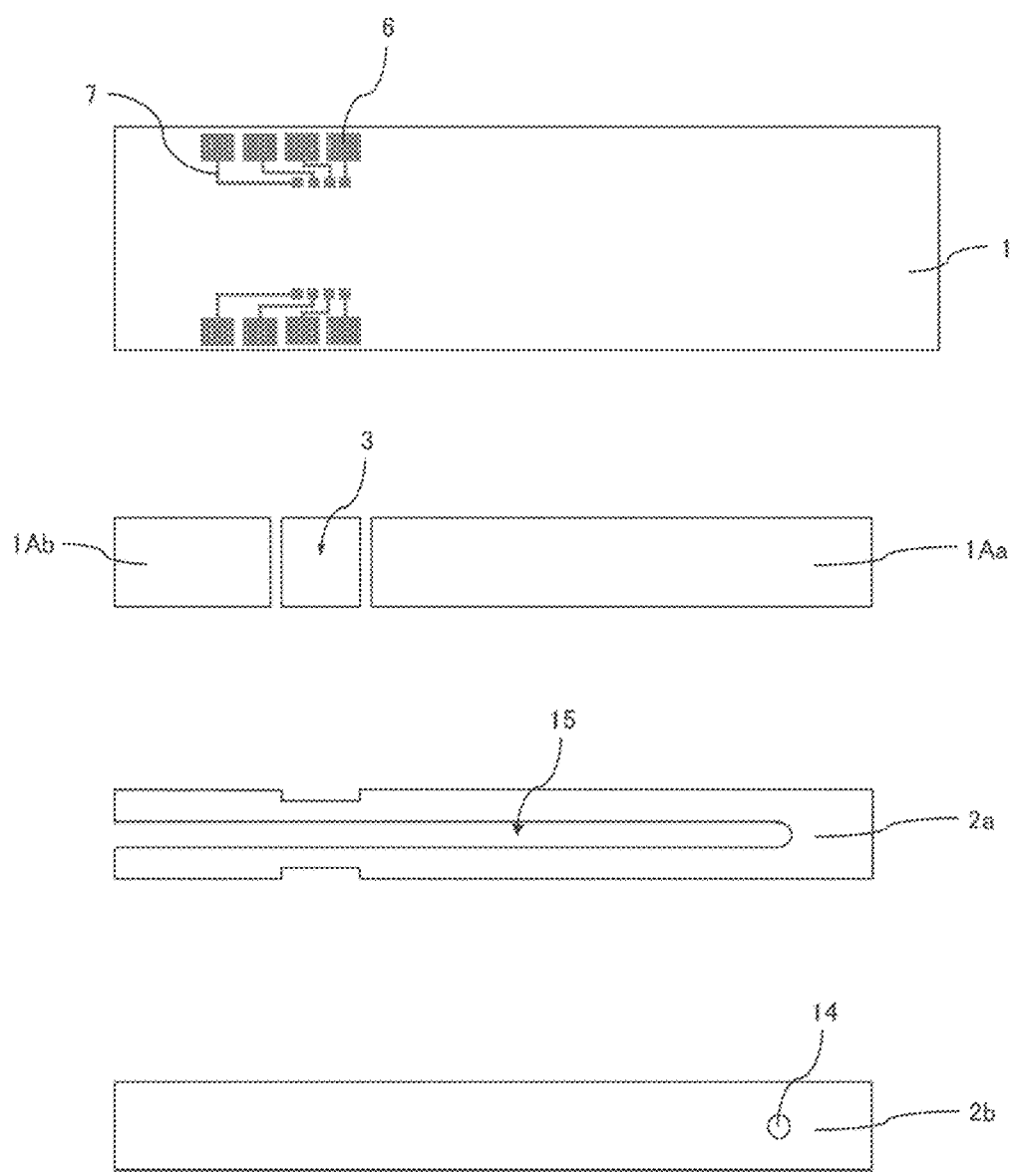
FIG. 2 is an exploded plan view showing the sensor apparatus shown in FIG. 1(a), in accordance with one embodiment of the invention.
Figure 3:
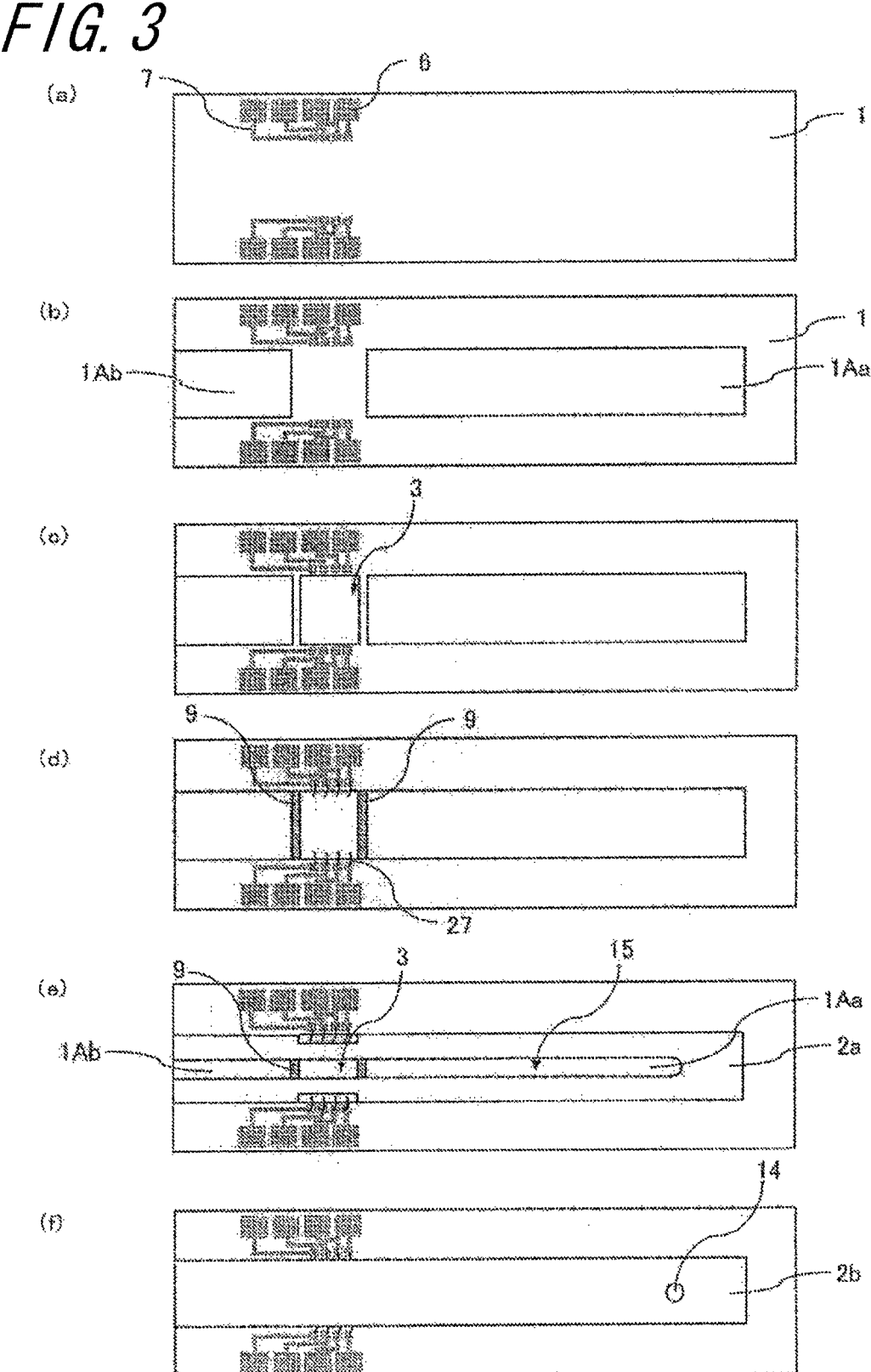
FIGS. 3(a)-3(f) illustrate various views of the sensor apparatus of FIG. 1(a) after various manufacturing process steps to produce the sensor apparatus shown in FIG. 1(a), in accordance with one embodiment of the invention.

A sensor apparatus 100 in accordance with a first embodiment of the invention will be described with reference to FIG. 1 to FIG. 3.

Figure 1:
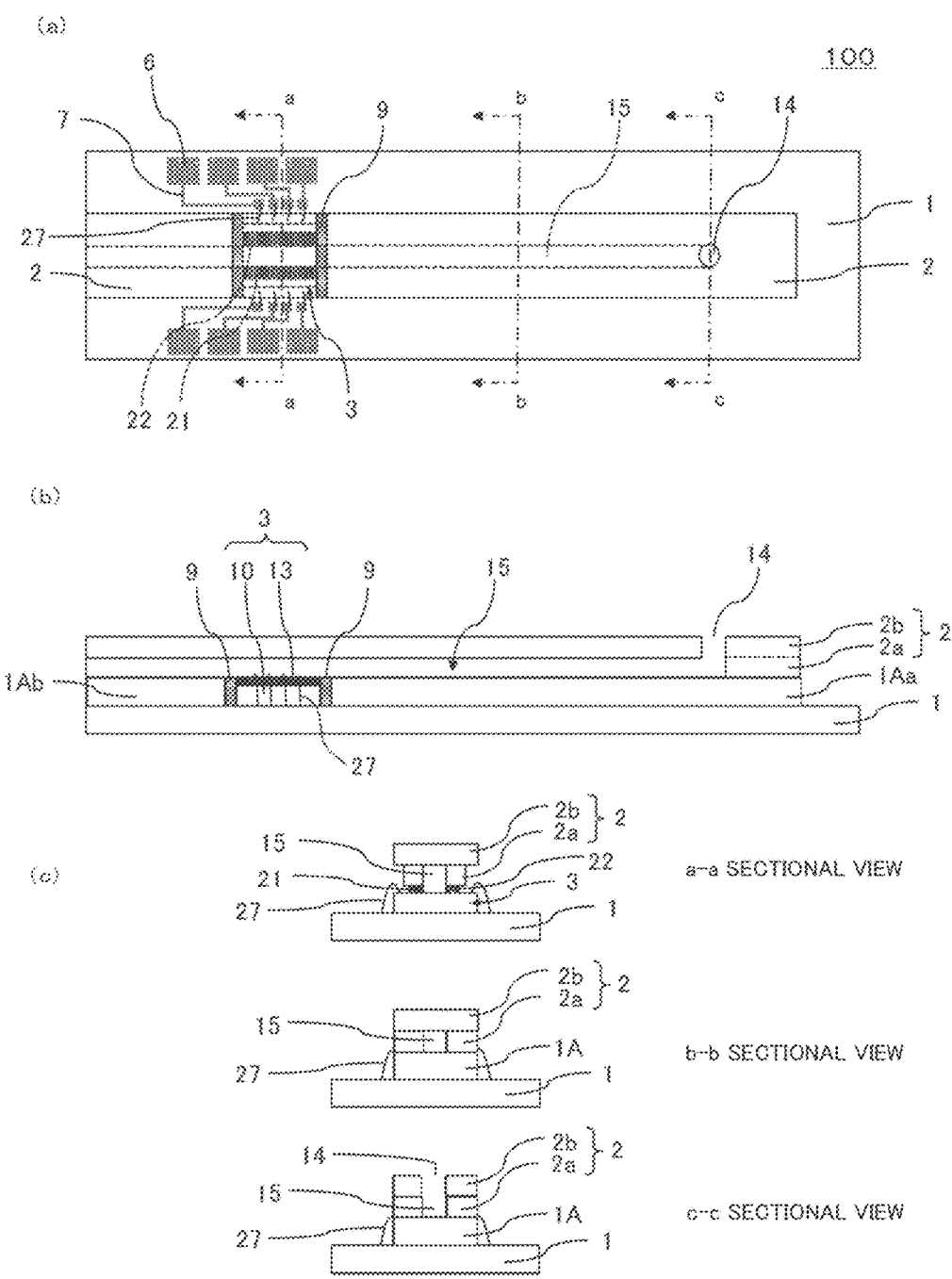
FIG. 1(a) is a plan view of a sensor apparatus in accordance with a first embodiment of the invention.
FIG. 1(b) is a lengthwise sectional view of the sensor apparatus of FIG. 1(a), in accordance with one embodiment of the invention.
FIG. 1(c) illustrates three widthwise sectional views of the sensor apparatus taken along lines a-a, b-b and c-c, respectively, of FIG. 1(a), in accordance with one embodiment of the invention.

As shown in FIG. 1, the sensor apparatus 100 of the present embodiment mainly comprises: a first cover member 1; an intermediate cover member 1A; a second cover member 2; a detection element 3; and a filler member 9.

As shown in FIG. 1(b), the first cover member 1 has a flat plate shape. For example, paper, plastics, celluloid, or ceramics can be used as the material for forming the first cover member 1.

As shown in FIG. 1(b), the detection element 3 comprises: an element substrate 10 located on an upper surface of the first cover member 1; and at least one detection portion 13 which is located on an upper surface of the element substrate 10 and detects an analyte.

As shown in FIG. 1(a), terminals 6 are arranged on the upper surface of the first cover member 1 so as to be electrically connected to the detection element 3.

In the present embodiment, as shown in FIG. 1(a), the intermediate cover member 1A is located on the upper surface of the first cover member 1 and has a space with the detection element 3. For example, a resin material such as acrylic resin or silicone resin is preferably used as the material for forming the intermediate cover member 1A. The first cover member 1 and the intermediate cover member 1A may be formed of different materials. It is preferable that the intermediate cover member 1A is greater in thickness than the detection element 3. As shown in FIG. 1(a) and FIG. 1(b), the filler member 9 is located in the space between the detection element 3 and the intermediate cover member 1A. The filler member 9 may be composed of a different material from the material constituting the intermediate cover member 1A and the element substrate 10, for example, a resin material such as PDMS. The filler member 9 does not necessarily have to be provided so as to completely fill the space between the detection element 3 and the intermediate cover member 1A, and may thus be applied only to a part corresponding to a flow passage 15, for example.

In the sensor apparatus of the present embodiment, the detection element and the intermediate cover member which constitutes at least a part of the flow passage are juxtaposed on the upper surface of the first cover member. This makes it possible to attain an analyte flow passage extending from an inlet to the detection portion even with the use of a detection element having a certain thickness, and thereby deliver an analyte, which has been wicked through the inlet by, for example, capillary phenomenon to the detection portion. That is, there is provided a sensor apparatus which incorporates a detection element having a certain thickness and yet includes, in itself, an analyte suction mechanism, and thus allows easy measurement operation. Moreover, the placement of the filler member between the detection element and the intermediate cover member in the space allows to suppress interference of capillary phenomenon based on the space, thus permitting smooth wicking of an analyte toward the detection element.

Moreover, in the present embodiment, the intermediate cover member 1A comprises a first portion 1Aa and a second portion 1Ab. As shown in FIG. 1(a), in a top view, the detection element 3 is located between the first portion 1Aa and the second portion 1Ab. In this case, when an analyte solution flows, through the first portion 1Aa which is a part of the flow passage 15, over the detection element 3, an excess of the analyte solution over that required for measurement operation flows toward the second portion 1Ab, thus permitting the supply of an adequate amount of the analyte solution to the detection element 3. In the presence of a space between the detection element 3 and the second portion 1Ab, the filler member 9 may be located in this space, too.

As shown in FIG. 1(b), the second cover member 2 is configured to cover at least a part of the detection element 3 and is joined to the intermediate cover member 1A. For example, a resin material such as acrylic resin or silicone resin is preferably used as the material for forming the second cover member 2. The first cover member 1 and the second cover member 2 may be formed of the same material. This helps reduce deformation resulting from the difference in thermal expansion coefficient between the first and second cover members. The second cover member 2 may either be joined only to the first cover member 1 or be joined to both of the first cover member 1 and the intermediate cover member 1A.

Figure 11:
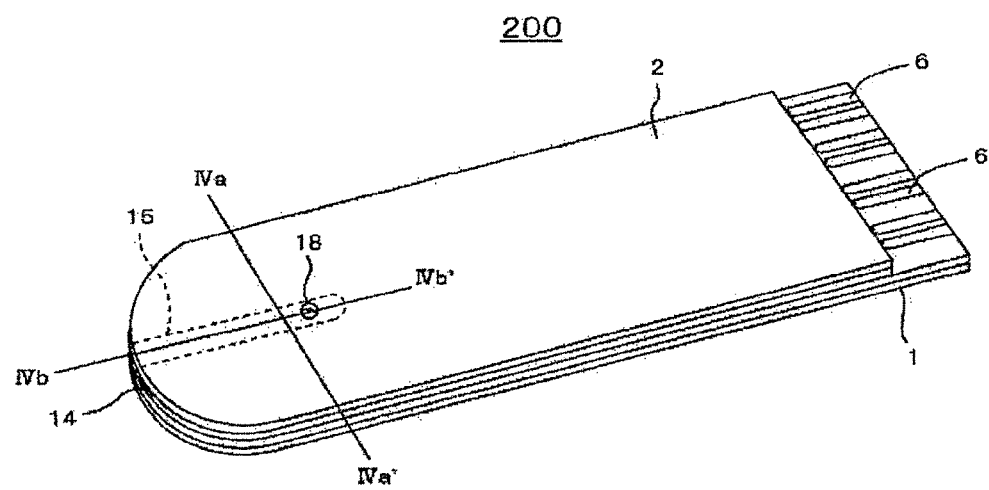
FIG. 11 is a perspective view of a sensor apparatus in accordance with a second embodiment of the invention, in accordance with one embodiment of the invention.
Figure 11:
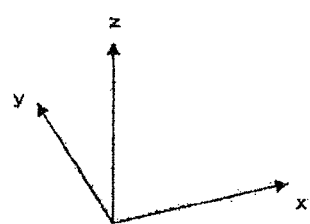

As shown in FIG. 1(b), the sensor apparatus 100 includes an inlet 14 into which an analyte flows, and a flow passage 15 which is continuous with the inlet 14, is surrounded by the intermediate cover member 1A and the second cover member 2, and extends at least to the detection portion 13. As shown in FIG. 1(c), the flow passage 15 is surrounded by the intermediate cover member 1A and the second cover member 2. In FIG. 1(c), there are shown the sections of the construction shown in FIG. 1(a), namely, in top-to-bottom order, a-a section, b-b section, and c-c section. As shown in FIG. 1(b), the inlet 14 passes through the second cover member 2 in a thickness direction thereof. The inlet 14 may be located on the side faces of the first and second cover members 1 and 2 as shown in FIG. 11.

In the present embodiment, as shown in FIG. 1, an electrode pattern is provided on the upper surface of the element substrate 13, and, protective members 21 and 22 are disposed so as to cover the electrode pattern. When a SAW element is used as the detection element 3, the electrode pattern corresponds to an IDT (InterDigital Transducer) electrode.

Next, modified examples of the sensor apparatus 100 of the first embodiment will be described.

Modified Example

Figure 4:
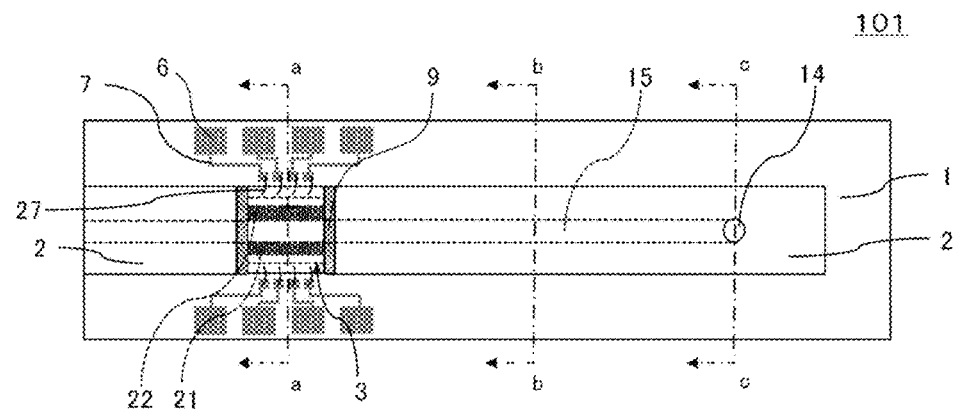
FIG. 4 is a plan view showing a modified example of the sensor apparatus shown in FIG. 1(a), in accordance with one embodiment of the invention.

FIG. 4 is a plan view showing a sensor apparatus 101 which is a modified example of the sensor apparatus 100 shown in FIG. 1.

The sensor apparatus 101 according to this modified example differs from the sensor apparatus 100 of the first embodiment in the arrangement of the terminals 6 relative to the detection element 3.

Specifically, in the sensor apparatus 100, as shown in FIG. 1, the terminals 6 are located toward an outlet 18 beyond the inlet 14-side end of the detection element 3. In contrast, in the sensor apparatus 101 according to this modified example, as shown in FIG. 4, at least a part of the terminals 6 is located toward the inlet 14 beyond the inlet 14-side end of the detection element 3.

In an arrangement of four terminals 6 lying on one side of the detection element 3 with respect to a longitudinal direction of the flow passage 15, wiring lines 7 connected to two outer terminals 6, respectively, have substantially the same length, and also wiring lines 7 connected to two inner terminals 6, respectively, have substantially the same length. This helps restrain signals obtained by the detection element 3 from varying depending on the length of the wiring line 7. Moreover, for example, by connecting one pair of the wiring lines 7 having substantially the same length to a part of the detection portion 13 of the detection element 3 which detects a target substance, and connecting the other pair of the wiring lines 7 having substantially the same length to a reference electrode for a target substance in the detection portion of the detection element 3, it is possible to reduce the aforementioned signal variations, and thereby afford higher detection reliability.

Figure 5:
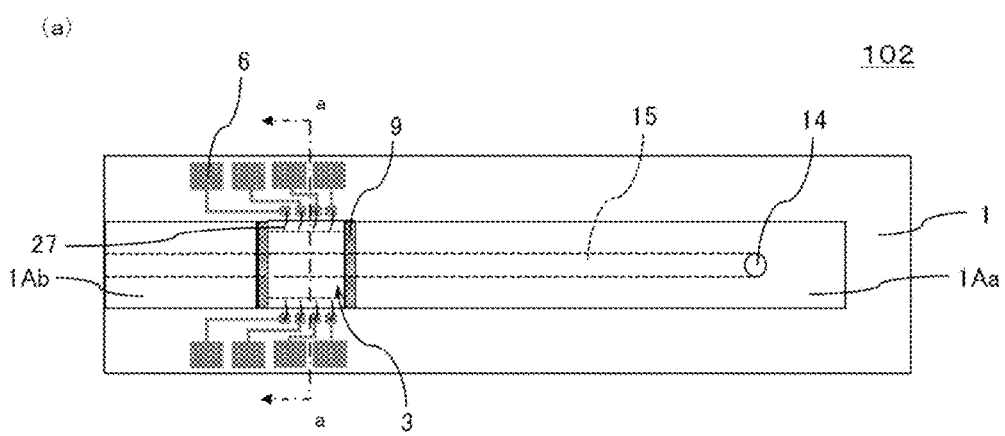
FIG. 5(a) is a plan view of a modified example of the sensor apparatus shown in FIG. 1(a), in accordance with one embodiment of the invention.
FIG. 5(b) is a lengthwise sectional view of the sensor apparatus of FIG. 5(a), in accordance with one embodiment of the invention.
FIG. 5(c) is a widthwise sectional view of the sensor apparatus taken along line 1-1 of FIG. 5(a), in accordance with one embodiment of the invention.
Figure 5:
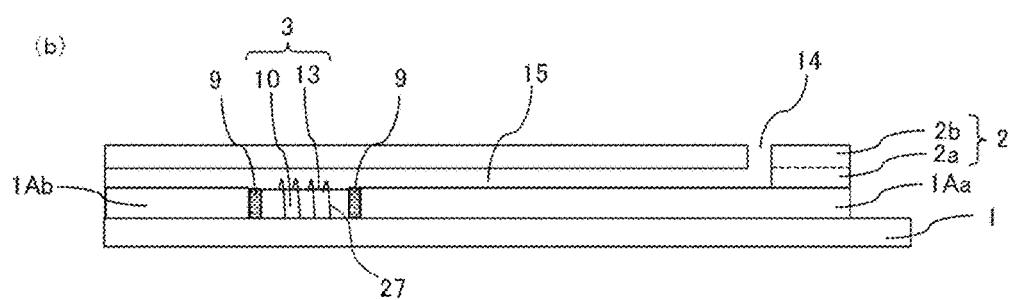
Figure 5:
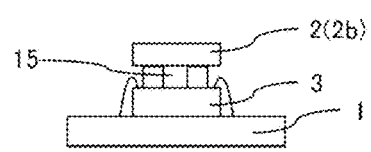

FIG. 5 is a view showing a sensor apparatus 102 which is a modified example of the sensor apparatus 100 shown in FIG. 1, and more specifically FIG. 5(a) is a plan view, FIG. 5(b) is a lengthwise sectional view, and FIG. 5(c) is a widthwise sectional view.

The sensor apparatus 102 according to this modified example differs from the sensor apparatus 100 of the first embodiment in that, as shown in FIG. 5, on the upper surface of the element substrate 13, the second cover member 2 is fixed directly onto, for example, IDT electrodes 11 and 12 without interposition of the protective members 21 and 22.

Figure 6:
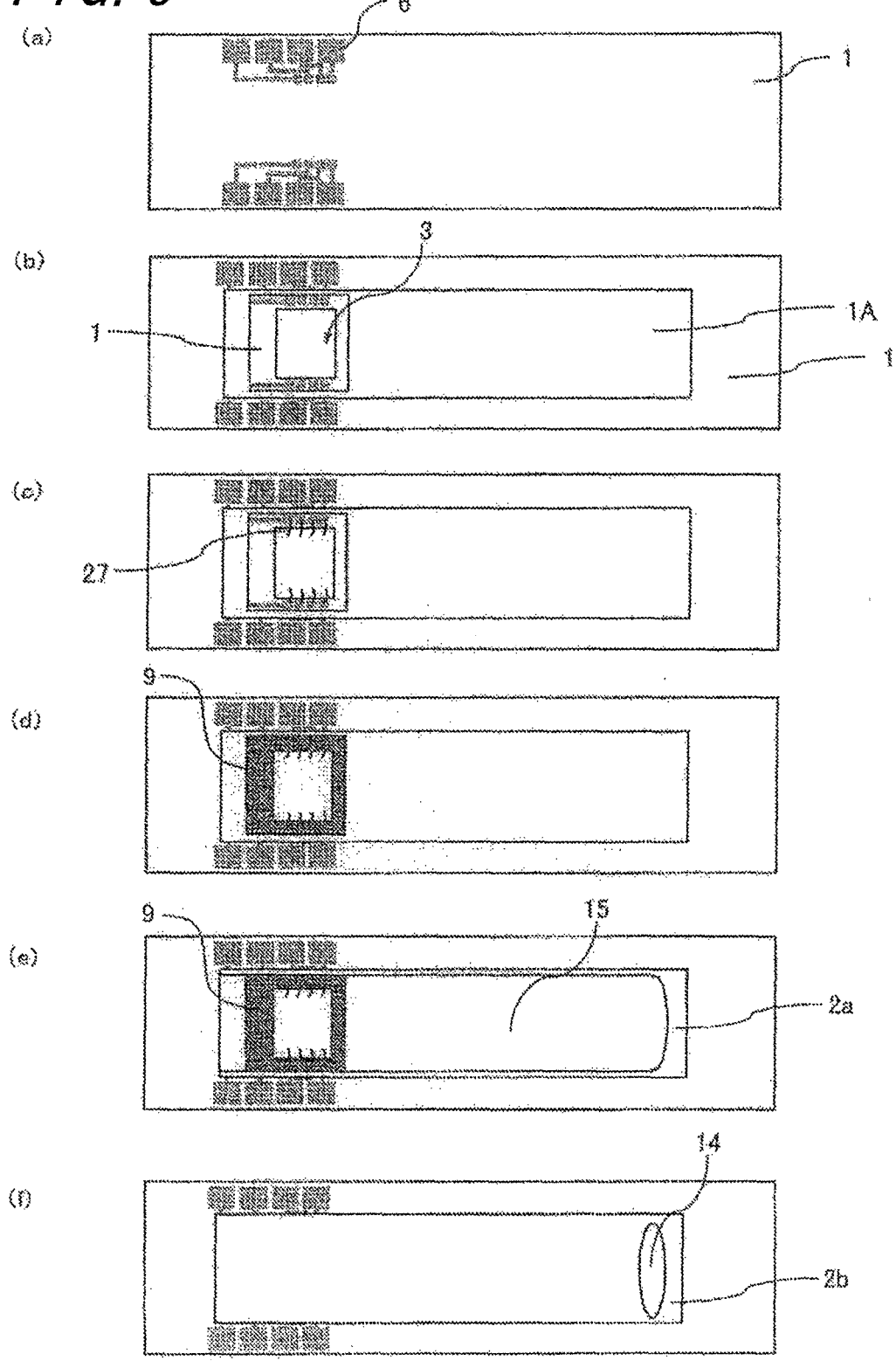
FIGS. 6(a)-6(f) illustrate various views of the sensor apparatus of FIG. 5(a) after various manufacturing process steps to produce the sensor apparatus shown in FIG. 5(a), in accordance with one embodiment of the invention.

FIG. 6 is a view of a sensor apparatus 103 which is a modified example of the sensor apparatus 100 shown in FIG. 1, illustrating manufacturing process steps in particular.

The sensor apparatus 103 according to this modified example differs from the sensor apparatus 100 of the first embodiment in that, in a top view, the detection element 3 is encircled by a second substrate 1b (intermediate cover member 1A) of the first cover member 1. As shown in FIG. 6(d) and FIG. 6(e), the filler member 9 is located between the detection element 3 and the intermediate cover member 1A in the space so as to surround the outer periphery of the detection element 3. This makes it possible to reduce the difference in level or a gap between the detection element 3 and a nearby part in the flow passage 15, and thereby allow an analyte to flow smoothly over the detection element 3. Moreover, in the region between the detection element 3 and the terminals 6, the filler member 9 covers a part of the wiring lines 7 and also a lead wire 27 for providing connection between the detection element 3 and the wiring line 7. This makes it possible to reduce a decrease in detection sensitivity caused by a contact between an analyte and the aforementioned constituent components.

In this modified example, after the formation of the intermediate cover member 1A and the detection element 3 as shown in FIG. 6(b), the detection element 3 and the wiring line 7 are connected to each other via the lead wire 27 as shown in FIG. 6(c). As an alternative, after the formation of the detection element 3 and the subsequent process of connecting the detection element 3 with the wiring line 7 via the lead wire 27, the intermediate cover member 1A is formed.

Figure 7:
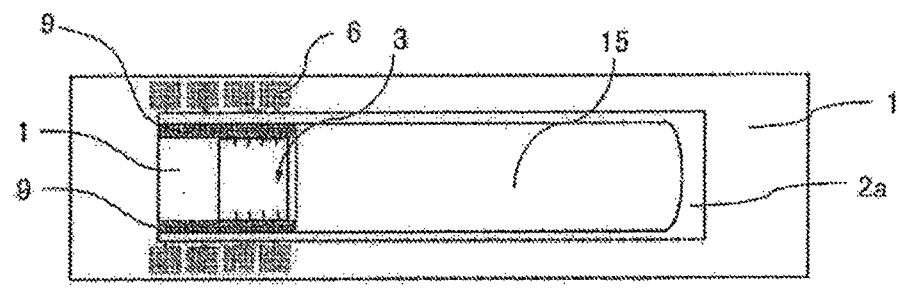
FIGS. 7(a)-7(b) illustrate plan views showing modified examples of the sensor apparatus shown in FIG. 1(a), corresponding to a manufacturing step as shown in FIG. 3(e), in accordance with one embodiment of the invention.
Figure 7:
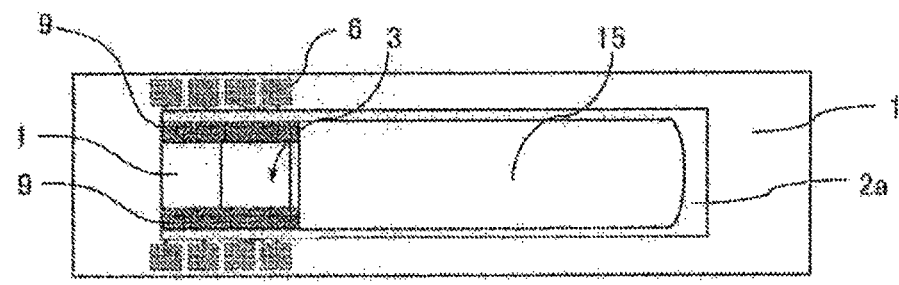

FIG. 7 is a plan view showing sensor apparatuses 104 and 105 that are modified examples of the sensor apparatus 100 shown in FIG. 1, and is a view corresponding to FIG. 3(e).

The sensor apparatuses 104 and 105 according to this modified example differ from the sensor apparatus 100 of the first embodiment in that, as shown in FIG. 7(a) and FIG. 7(b), the filler member 9 is located so as to extend along the longitudinal direction of the flow passage 15 in the range of a space between the detection element 3 and the intermediate cover member 1A. This makes it possible to reduce the difference in level or a gap between the detection element 3 and a part located on each side thereof, and thereby allow an analyte to flow laterally to the detection element 3 smoothly. Moreover, in the region between the detection element 3 and the terminals 6, the filler member 9 covers a part of the wiring lines 7 and also the lead wire 27 for providing connection between the detection element 3 and the wiring line 7. This makes it possible to reduce a decrease in detection sensitivity caused by a contact between an analyte and the aforementioned constituent components.

Moreover, as shown in FIG. 7(b), in addition to being located between the detection element 3 and the intermediate cover member 1A in the space, the filler member 9 may also be located so as to cover a part of the lead wire 27 for providing connection between the detection element 3 and the wiring line 7 which lies on the upper surface of the detection element 3 (element substrate 10). This makes it possible to achieve further reduction of a decrease in detection sensitivity caused by a contact between an analyte and the lead wire 27.

Figure 8:
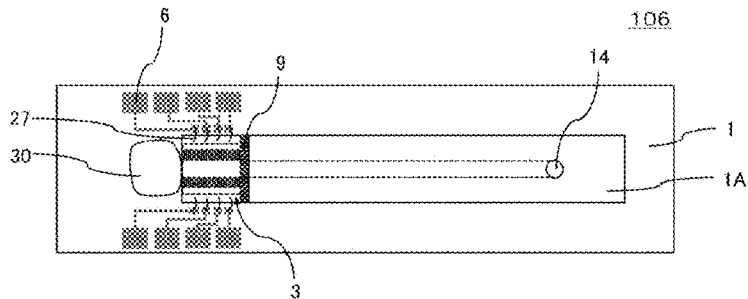
FIG. 8(a) is a plan view showing a modified example of the sensor apparatus shown in FIG. 1(a), in accordance with one embodiment of the invention.
FIG. 8(b) is a lengthwise sectional view of the sensor apparatus of FIG. 8(a), in accordance with one embodiment of the invention.
Figure 8:
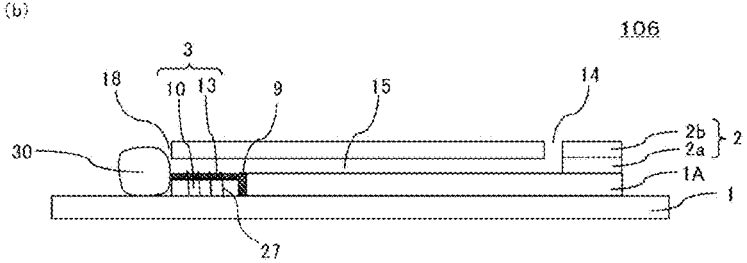

FIG. 8 is a view showing a sensor apparatus 106 which is a modified example of the sensor apparatus 100 shown in FIG. 1, and more specifically FIG. 8(a) is a plan view and FIG. 8(b) is a lengthwise sectional view.

The sensor apparatus 106 according to this modified example includes, instead of the second portion 1Ab of the intermediate cover member 1A of the sensor apparatus 100 of the first embodiment, a liquid absorbing member 30 located on the upper surface of the first cover member 1 and lying in a position opposite the intermediate cover member 1A with respect to the detection element 3. The placement of the liquid absorbing member 30 permits absorption of an excess of an analyte solution, renders the amount of an analyte solution flowing over the detection portion 13 uniform throughout the detection portion 13, and achieves measurement operation with stability.

For example, a porous material such as cellulose nitrate can be used as the material for forming the liquid absorbing member 30.

In this modified example, the liquid absorbing member 30 is spaced slightly away from an end of the flow passage 15. In this case, a gap between them serves as the outlet 18, wherefore capillary phenomenon can be exploited effectively.

Figure 9:
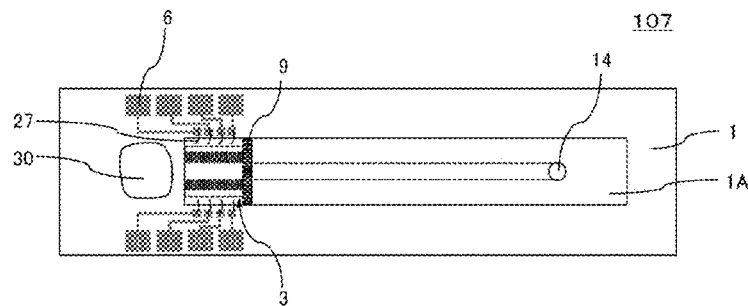
FIG. 9(a) is a plan view showing a modified example of the sensor apparatus shown in FIG. 1(a), in accordance with one embodiment of the invention.
FIG. 9(b) is a lengthwise sectional view of the sensor apparatus of FIG. 9(a), in accordance with one embodiment of the invention.
Figure 9:
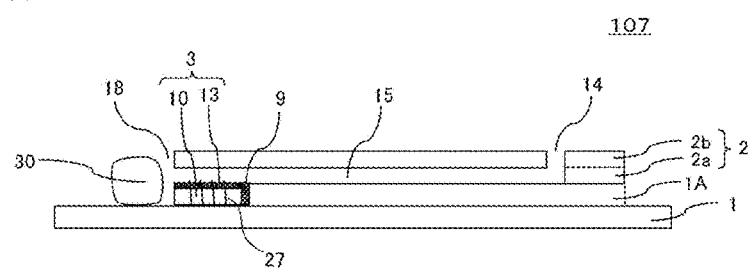

FIG. 9 is a view showing a sensor apparatus 107 which is a modified example of the sensor apparatus 100 shown in FIG. 1, and more specifically FIG. 9(a) is a plan view and FIG. 9(b) is a lengthwise sectional view.

The sensor apparatus 107 according to this modified example differs from the sensor apparatus 106 shown in FIG. 8 in that, as shown in FIG. 9, the liquid absorbing member 30 is located on the upper surface of the first cover member 1 and lies in a position opposite the intermediate cover member 1A with respect to the detection element 3, with a spacing left between the liquid absorbing member 30 and the detection element 3. In this case, after passing over the upper surface of the detection element 3, an analyte flowing through the flow passage 15 is absorbed by the liquid absorbing member 30. This makes it possible to absorb the analyte which has undergone detection on the upper surface of the detection element 3.

Figure 10:
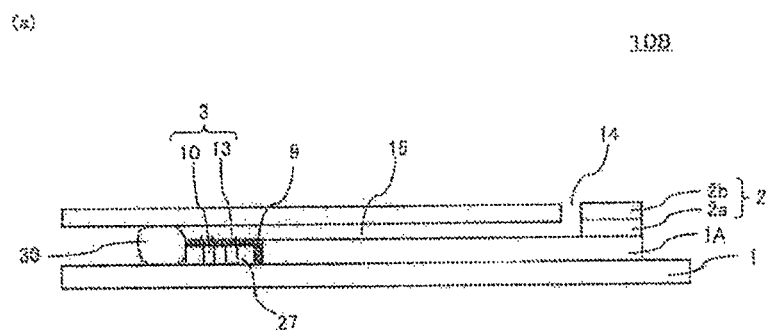
FIGS. 10(a) and 10(b) illustrate lengthwise sectional views of modified examples of the sensor apparatus shown in FIG. 1(a), in accordance with one embodiment of the invention.
Figure 10:
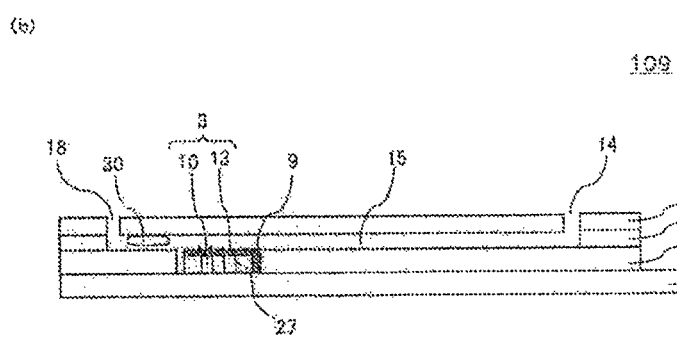

FIG. 10 is a lengthwise sectional view showing sensor apparatuses 108 and 109 that are modified examples of the sensor apparatus 100 shown in FIG. 1.

The sensor apparatus 108 according to this modified example differs from the sensor apparatus 106 shown in FIG. 8 in that, as shown in FIG. 10(a), the liquid absorbing member 30 contacts both of the upper surface of the first cover member 1 and the lower surface of the second cover member 2, namely the upper and lower surfaces of the flow passage 15. This makes it possible to, as described above, permit absorption of an excess of an analyte solution, render the amount of an analyte solution flowing over the detection portion 13 uniform throughout the detection portion 13, and achieve measurement operation with stability. Moreover, adjustment of the porosity of the liquid absorbing member 30 allows the porous liquid absorbing member 30 to serve as the outlet 18. In this case, by disposing the liquid absorbing member 30 so as to contact, in addition to the upper and lower surfaces of the flow passage 15 as described above, a side wall of the flow passage 15, the flow passage 15 is blocked by the liquid absorbing member 30.

The sensor apparatus 109 according to this modified example differs from the sensor apparatus 106 shown in FIG. 8 in that, as shown in FIG. 10(b), the liquid absorbing member 30 contacts the upper surface of the first cover member 1 alone. In this case, the liquid absorbing member 30 exhibits the capability of drawing an analyte flowing through the flow passage 15 upon contacting it, for example, and is thus able to direct the analyte toward the upper surface of the detection element 3 located ahead in a direction in which the analyte flows.

In the sensor apparatus 100 of the first embodiment and the modified examples thereof thus far described, although there is no detailed description as to the detection element 3, etc., the configuration of a sensor apparatus according to each embodiment as will hereafter be described can be applied either in an as-is state or in a form adapted to the foregoing sensor apparatuses.

Second Embodiment

Next, a sensor apparatus 200 in accordance with a second embodiment of the invention will be described with reference to FIG. 11 to FIG. 16.

The sensor apparatus 200 mainly comprises: a first cover member 1; a second cover member 2; and a detection element 3. The first cover member 1 includes a first substrate 1a and a second substrate 1b laminated on the first substrate 1a, and the second cover member 2 includes a third substrate 2a laminated on the second substrate 1b and a fourth substrate 2b laminated on the third substrate 2a. The detection element 3, which is a surface acoustic wave element, mainly comprises: an element substrate 10; a first IDT electrode 11; a second IDT electrode 12; and a detection portion 13 (refer to FIG. 15).

Figure 14:
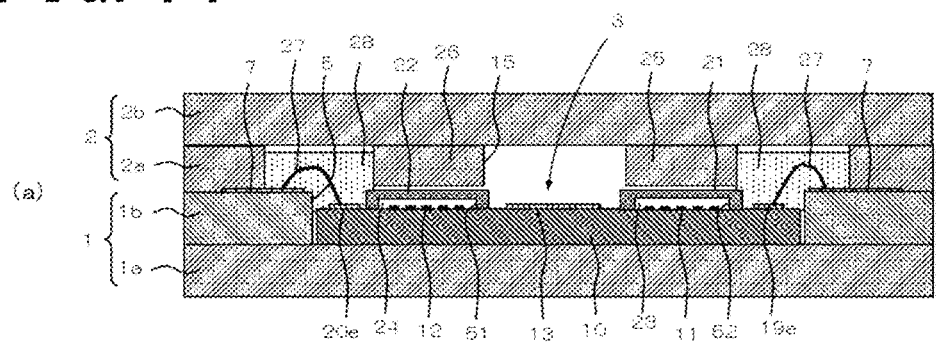
FIG. 14(a) is a sectional view taken along the line IVa-IVa' shown in FIG. 11, in accordance with one embodiment of the invention.
FIG. 14(b) is a sectional view taken along the line IVb-IVb' shown in FIG. 11, in accordance with one embodiment of the invention.
Figure 14:
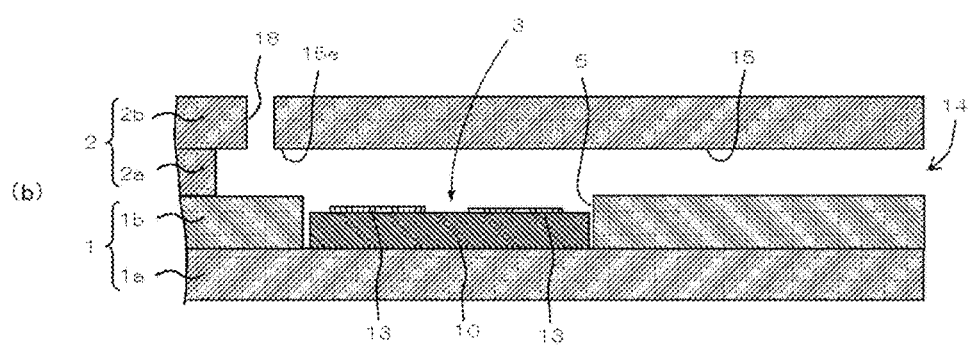

The first cover member 1 and the second cover member 2 are bonded to each other, and the detection element 3 is stored in an interior region between the bonded first and second cover members 1 and 2. As shown in FIG. 14 which is a sectional view, the first cover member 1 has, in an upper surface thereof, an element storage recess 5 in which the detection element 3 is located.

As shown in FIG. 11, the second cover member 2 has, at an end thereof in a longitudinal direction (x direction), an inlet 14 which is an inflow port for an analyte solution, and also has a groove 15 extending from the inlet 14 to a location immediately above the detection element 3. In FIG. 11, the groove 15 is represented by a broken line to indicate its position.

Figure 12:
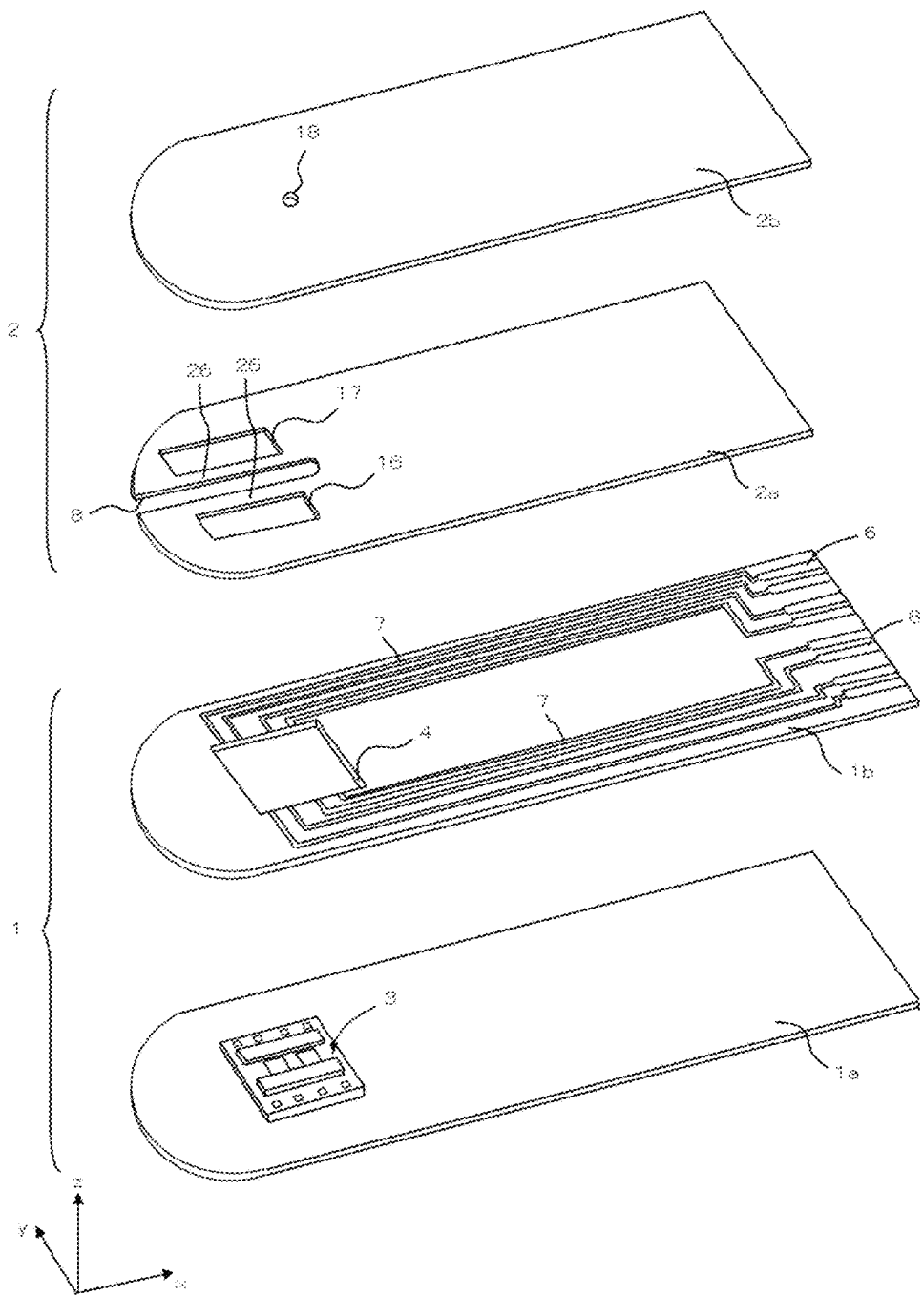
FIG. 12 is an exploded perspective view of the sensor apparatus shown in FIG. 11, in accordance with one embodiment of the invention.

FIG. 12 is an exploded perspective view of the first cover member 1 and the second cover member 2.

First Cover Member

The first substrate 1a constituting the first cover member 1 is formed as a flat plate having a thickness of 0.1 mm to 0.5 mm, for example. In a plan view, the first substrate 1a is substantially rectangular-shaped, but one end thereof in the longitudinal direction is curved outwardly in an arcuate form. The length of the first substrate 1a in the x direction falls in the range of 1 cm to 5 cm, for example, whereas the length thereof in the y direction falls in the range of 1 cm to 3 cm, for example.

The second substrate 1b is laminated on an upper surface of the first substrate 1a. The second substrate 1b is formed in a flat frame shape by creating a recess-forming through hole 4 in a flat plate. The thickness of the second substrate 1b falls in the range of 0.1 mm to 0.5 mm, for example. In a plan view, the second substrate 1b is substantially identical with the first substrate 1a in outer shape, as well as in length in the x and y directions.

The second substrate 1b having the recess-forming through hole 4 and the flat plate-shaped first substrate 1a join to provide the element storage recess 5 in the first cover member 1. That is, the upper surface of the first substrate 1a located inside the recess-forming through hole 4 becomes the bottom surface of the element storage recess 5, and the inner wall of the recess-forming through hole 4 becomes the inner wall of the element storage recess 5.

Moreover, an upper surface of the second substrate 1b is formed with a terminal 6 and a wiring line 7 routed from the terminal 6 to the recess-forming through hole 4. The terminal 6 is formed on the upper surface of the other end of the second substrate 1b in the x direction. In setting the sensor apparatus 200 in external measuring equipment (not shown in the drawing), only this terminal 6-bearing part is actually inserted into the equipment, that is; the sensor apparatus 200 is electrically connected to the external measuring equipment via the terminal 6. Moreover, the terminal 6 and the detection element 3 are electrically connected to each other via, for example, the wiring line 7. A signal issued from the external measuring equipment is inputted, through the terminal 6, to the sensor apparatus 200, and, a signal issued from the sensor apparatus 200 is inputted, through the terminal 6, to the external measuring equipment.

Second Cover Member

The second cover member 2 is joined to the upper surface of the first cover member 1 composed of the first substrate 1a and the second substrate 1b. The second cover member 2 includes the third substrate 2a and the fourth substrate 2b.

The third substrate 2a is bonded to the upper surface of the second substrate 1b. The third substrate 2a is formed as a flat plate having a thickness of 0.1 mm to 0.5 mm, for example. In a plan view, the third substrate 2a is substantially rectangular-shaped, but, like the first and second substrates 1a and 1b, one end thereof in the longitudinal direction is curved outwardly in an arcuate form. The length of the third substrate 2a in the x direction is adjusted to be slightly shorter than the length of the second substrate 1b in the x direction, for example, in the range of 0.8 cm to 4.8 cm, to uncover the terminal 6 of the second substrate 1b. Like the first and second substrates 1a and 1b, the length of the third substrate 2a in the y direction falls in the range of 1 cm to 3 cm, for example.

A cutaway 8 is formed in the third substrate 2a. The cutaway 8 is formed by cutting the third substrate 2a so as to extend from the vertex of the accurately-curved one end toward the other end in the x direction, as well as to pass through the third substrate 2a in a thickness direction thereof. The cutaway 8 is intended for the formation of the groove 15. On both sides of the cutaway 8 in the third substrate 2a, there are provided a first through hole 16 and a second through hole 17 passing thickness wise through the third substrate 2a. When the third substrate 2a overlies the second substrate 1b, the part of connection between the detection element 3 and the wiring line 7 is located inside the first through hole 16 and the second through hole 17. As will hereafter be described, an area between the first through hole 16 and the cutaway 8 in the third substrate 2a serves as a first partition portion 25 for separating the groove 15 and a space defined by the first through hole 16. Moreover, an area between the second through hole 17 and the cutaway 8 in the third substrate 2a serves as a second partition portion 26 for separating the groove 15 and a space defined by the second through hole 17.

The fourth substrate 2b is bonded to an upper surface of the third substrate 2a. The fourth substrate 2b is formed as a flat plate having a thickness of 0.1 mm to 0.5 mm, for example. In a plan view, the fourth substrate 2b is substantially identical with the third substrate 2a in outer shape, as well as in length in the x and y directions. The fourth substrate 2b is joined to the third substrate 2a having the cutaway 8, thus providing the groove 15 at the lower surface of the second cover member 2. That is, the lower surface of the fourth substrate 2b located inside the cutaway 8 becomes the bottom surface of the groove 15, and the inner wall of the cutaway 8 becomes the inner wall of the groove 15. The groove 15 extends from the inlet 14 to, at least, a location immediately above the detection portion 13, and has a rectangular sectional profile, for example.

The fourth substrate 2b is formed with an outlet 18 which is a hole passing thickness wise there through. When the fourth substrate 2b overlies the third substrate 2a, the outlet 18 is located above the end of the cutaway 8. Thus, the end of the groove 15 is continuous with the outlet 18. The outlet 18 is provided to let, for example, air within the groove 15 go out.

The outlet 18 may be given any shape which is capable of release of air within the flow passage, such as a cylindrical shape or a quadrangular prism shape. Note that formation of an outlet 18 having too large a planar configuration leads to an increase in the area of an analyte solution filled in the flow passage exposed to outside air, thus causing an evaporation of water from the analyte solution. In consequence, the analyte solution is prone to changes in concentration that will result in poor measurement accuracy. In view of this, the outlet 18 is configured so as not to have an unnecessarily large planar configuration. Specifically, in a cylindrical outlet 18, a diameter thereof is less than or equal to 1 mm, whereas, in a quadrangular prism-shaped outlet 18, each side thereof has a length of less than or equal to 1 mm.

Moreover, the outlet 18 has a hydrophobic inner wall. This helps restrain an analyte solution filled in the flow passage from leaking to outside from the outlet 18.

The first substrate 1a, the second substrate 1b, the third substrate 2a, and the fourth substrate 2b are formed of, for example, paper, plastics, celluloid, or ceramics. These substrates may be formed of the same material. The substrates formed of the same material are substantially uniform in thermal expansion coefficient. This helps reduce deformation resulting from the difference in thermal expansion coefficient among the substrates. Moreover, there may be a case where a biomaterial is put on the detection portion 13, and, among biomaterials, some are susceptible to quality deterioration under application of external light such as ultraviolet rays. In this case, it is advisable to use an opaque material having light-blocking capability for the first cover member 1 and the second cover member 2. On the other hand, for a case where external light-induced quality deterioration hardly occurs in the detection portion 13, the second cover member 2 having the groove 15 may be formed of a nearly transparent material. This permits visual check of the condition of an analyte solution flowing through the interior of the flow passage.

Detection Element 3

The following describes the detection element 3.

Figure 15:
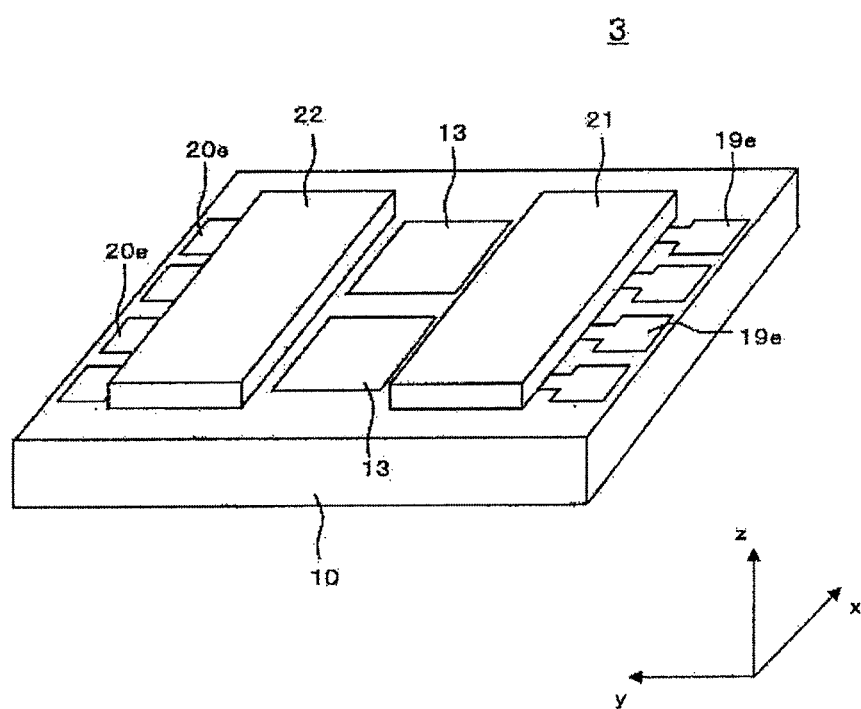
FIG. 15 is a perspective view of a detection element used in the sensor apparatus shown in FIG. 11, in accordance with one embodiment of the invention.
Figure 16:
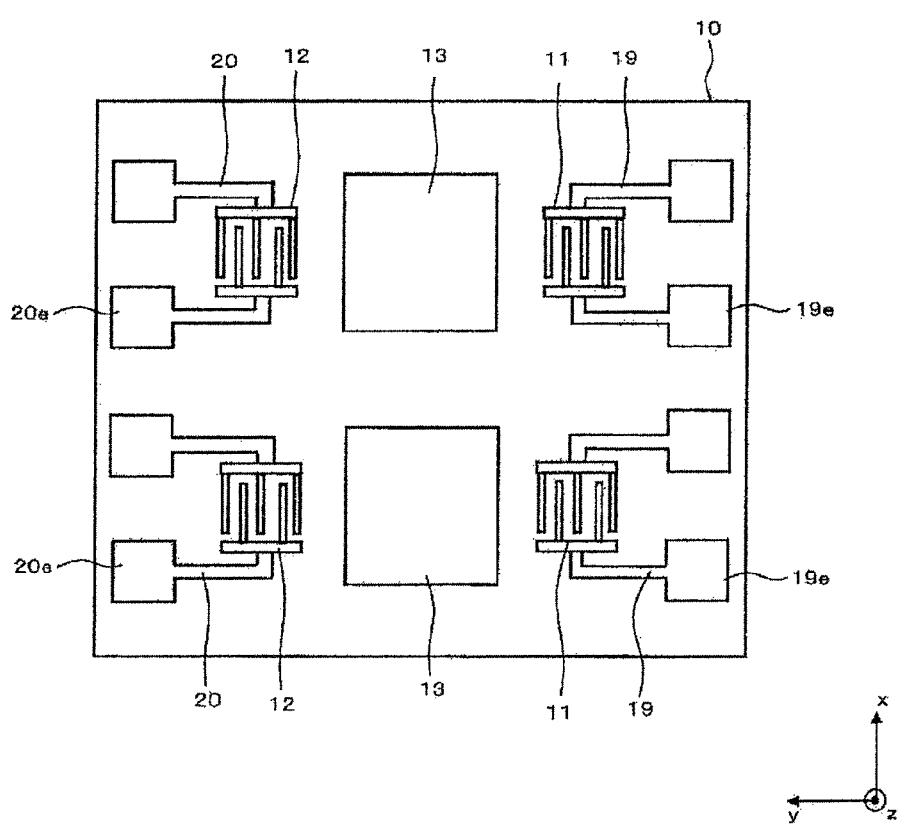
FIG. 16 is a plan view of the detection element shown in FIG. 15, with a first protective member and a second protective member removed, in accordance with one embodiment of the invention.

FIG. 15 is a perspective view of the detection element 3, and FIG. 16 is a plan view of the detection element 3, with the first protective member 21 and the second protective member 22 removed. The detection element 3 comprises: the element substrate 10; the detection portion 13 located on the upper surface of the element substrate 10; the first IDT electrode 11; the second IDT electrode 12; a first extraction electrode 19; and a second extraction electrode 20.

The element substrate 10 is constructed of a substrate formed of a single crystal having piezoelectric properties, such for example as lithium tantalate ($LiTaO_3$) single crystal, lithium niobate ($LiNbO_3$) single crystal or crystal. The planar configuration and dimensions of the element substrate 10 are determined as appropriate. By way of example, the element substrate 10 has a thickness of 0.3 mm to 1 mm.

As shown in FIG. 16, the first IDT electrode 11 comprises a pair of comb-like electrodes. Each of the comb-like electrodes includes two opposed bus bars, a plurality of electrode fingers extending from one bus bar to the other bus bar, and a plurality of electrode fingers extending from the other bus bar to one bus bar. The paired comb-like electrodes are arranged so that their electrode fingers are interdigitated. The second IDT electrode 12 is of similar construction to the first IDT electrode 11. The first IDT electrode 11 and the second IDT electrode 12 constitute a transversal IDT electrode.

The first IDT electrode 11 is intended for generation of a predetermined SAW (Surface Acoustic Wave), and the second IDT electrode 12 is intended for reception of the SAW produced by the first IDT electrode 11. The first IDT electrode 11 and the second IDT electrode 12 are located on the same straight line to allow the second IDT electrode 12 to receive the SAW produced by the first IDT electrode 11. The design of frequency response characteristics is based on the number of the electrode fingers of the first IDT electrode 11 and the second IDT electrode 12, the distance between the adjacent electrode fingers, the crossing width of the electrode fingers, etc., serving as parameters. SAWs of various vibration modes are excited by IDT electrodes. For example, the vibration mode of a transversal wave called SH wave is utilized in the detection element 3.

Moreover, an elastic member may be disposed externally of the first IDT electrode 11 and the second IDT electrode 12 in the direction of SAW propagation (y direction) to reduce SAW reflection. The frequency of SAW can be set within the range of several megahertz (MHz) to several gigahertz (GHz), for example. It is advisable to set the SAW frequency within the range of several hundred MHz to 2 GHz as a matter of practicality, and, in this case, downsizing of the detection element 3 can be achieved, thus making the sensor apparatus 200 compact.

The first extraction electrode 19 is connected to the first IDT electrode 11, and the second extraction electrode 20 is connected to the second IDT electrode 12. The first extraction electrode 19 is extracted from the first IDT electrode 11 in the opposite direction to the detection portion 13, and an end 19e of the first extraction electrode 19 is electrically connected to the wiring line 7 disposed in the first cover member 1. The second extraction electrode 20 is extracted from the second IDT electrode 12 in the opposite direction to the detection portion 13, and an end 20e of the second extraction electrode 20 is electrically connected to the wiring line 7.

The first IDT electrode 11, the second IDT electrode 12, the first extraction electrode 19, and the second extraction electrode 20 are formed of, for example, aluminum or an alloy of aluminum and copper. Moreover, these electrodes may be given a multilayer form. In the multilayer electrode, for example, the first layer is formed of titanium or chromium, and the second layer is formed of aluminum or an aluminum alloy.

The first IDT electrode 11 and the second IDT electrode 12 are covered with a protective film (not shown). The protective film is conducive to, for example, protection of the first IDT electrode 11 and the second IDT electrode 12 against oxidation. The protective film is formed of, for example, silicon oxide, aluminum oxide, zinc oxide, titanium oxide, silicon nitride, or silicon. The thickness of the protective film is about 1/10 of the thickness of the first and second IDT electrodes 11 and 12 (10 to 30 nm). The protective film may be formed over the entire area of the upper surface of the element substrate 10, with the end 19e of the first extraction electrode 19 and the end 20e of the second extraction electrode 20 left exposed.

The detection portion 13 lies between the first IDT electrode 11 and the second IDT electrode 12. For example, the detection portion 13 is composed of a metal film, and an aptamer which is immobilized on the surface of the metal film and is formed of nucleic acid or peptide. For example, the metal film has a double-layer form including chromium and a gold film formed on the chromium. The detection portion 13 undergoes reaction with a target substance contained in an analyte solution. Specifically, upon contact of an analyte solution with the detection portion 13, a specific target substance contained in the analyte solution is bound to the corresponding aptamer.

Given that the first IDT electrode 11, the second IDT electrode 12, and the detection portion 13 arranged along the y direction are grouped into a set, then the sensor apparatus 200 is provided with two such sets. In this case, the detection portion 13 of one of the sets and the detection portion 13 of the other may undergo reactions with different target substances, that is; two different substances can be detected by a single sensor apparatus.

As shown in FIG. 15, the first IDT electrode 11 is covered with the first protective member 21. The first protective member 21 is located on the upper surface of the element substrate 10, and has, as shown in FIG. 14(a), a first recess 51 opening into the upper surface of the element substrate 10. With the first protective member 21 located on the upper surface of the element substrate 10, a region enclosed by the inner surface of the first recess 51 and the upper surface of the element substrate 10 is defined as a first vibration space 23. The first IDT electrode 11 is hermetically sealed in the first vibration space 23. This makes it possible to isolate the first IDT electrode 11 from outside air and an analyte solution, and thereby provide protection for the first IDT electrode 11. Moreover, the provision of the first vibration space 23 helps suppress deterioration of the characteristics of SAW excited by the first IDT electrode 11.

Likewise, the second IDT electrode 12 is covered with the second protective member 22. The second protective member 22 is also located on the upper surface of the element substrate 10, and has, as shown in FIG. 14(a), a second recess 52 opening into the upper surface of the element substrate 10. With the second protective member 22 located on the upper surface of the element substrate 10, a region enclosed by the inner surface of the second recess 52 and the upper surface of the element substrate 10 is defined as a second vibration space 24. The second IDT electrode 12 is hermetically sealed in the second vibration space 24. This makes it possible to isolate the second IDT electrode 12 from outside air and an analyte solution, and thereby provide protection for the second IDT electrode 12. Moreover, the provision of the second vibration space 24 helps suppress deterioration of the characteristics of SAW received by the second IDT electrode 12.

The first protective member 21 is composed of an annular frame body secured to the upper surface of the element substrate 10 so as to surround two first IDT electrodes 11 arranged along the x direction, and a lid body secured to the frame body so as to block the opening of the frame body. For example, this structure can be formed by making a resin film from a photosensitive resin material, and performing patterning on the resin film by means of photolithography or otherwise. The second protective member 21 can be constructed in a similar way.

Although two first IDT electrodes 11 are covered with a single first protective member 21 in the sensor apparatus 200, alternatively, the two first IDT electrodes 11 may be each separately covered with a single first protective member 21. In another alternative, the two first IDT electrodes 11 are covered with a single first protective member 21, and a partition is provided between the two first IDT electrodes 11. Likewise, two second IDT electrodes 12 may be each separately covered with a single second protective member 22, or alternatively the second IDT electrodes 12 are covered with a single second protective member 22, and a partition is provided between the two second IDT electrodes 12.

In conducting analyte solution detection in the detection element 3 that utilizes SAW, at first, a predetermined voltage from external measuring equipment is applied to the first IDT electrode 11 via the wiring line 7 and the first extraction electrode 19, for example. Then, SAW having a predetermined frequency is produced within the first IDT electrode 11-bearing region. Part of the thereby produced SAW propagates toward the detection portion 13, passes through the detection portion 13, and reaches the second IDT electrode 12. In the detection portion 13, the aptamer of the detection portion 13 is bound to a specific target substance contained in an analyte solution, and the weight of the detection portion 13 changes correspondingly, with consequent variations in the characteristics, such as the phase, of the SAW passing under the detection portion 13. In response to the arrival of the SAW which has undergone such characteristic variations, a corresponding voltage is developed in the second IDT electrode. This voltage is put out through the second extraction electrode 20 and the wiring line 7, for example. The properties and ingredients of the analyte solution can be examined by checking a readout on the outputted voltage provided by the external measuring equipment.

In the sensor apparatus 200, capillary phenomenon is utilized to direct an analyte solution to the detection portion 13. Specifically, when the second cover member 2 is joined to the first cover member 1, the groove 15 formed in the lower surface of the second cover member 2 constitutes a narrow elongate tube. Thus, the size such as the width or the diameter of the groove 15 is set at a predetermined value in consideration of, for example, the type of an analyte solution and the constituent materials of the first and second cover members 1 and 2, so that capillary phenomenon can be caused in the narrow elongate tube constituted by the groove 15. The width (the dimension in the y direction) of the groove 15 falls in the range of 0.5 mm to 3 mm, for example, and, the depth (the dimension in the z direction) of the groove 15 falls in the range of 0.1 mm to 0.5 mm, for example. The groove 15 has an extension 15e which is a part extended beyond the detection portion 13, and, the second cover member 2 is formed with the outlet 18 which is continuous with the extension 15e. When an analyte solution is introduced into the flow passage, air present in the flow passage is expelled through the outlet 18.

By virtue of such a tube capable of causing capillary phenomenon formed in the cover member comprising the first cover member 1 and the second cover member 2, upon contacting the inlet 14, an analyte solution can be readily drawn into the cover member while passing through the groove 15 serving as a flow passage. Thus, the sensor apparatus 200 in itself has an analyte-solution suction mechanism, and is therefore capable of suction of an analyte solution without the necessity of using an instrument such as a pipette. Moreover, the part where the inlet 14 is formed is rounded, and the inlet 14 is located at the vertex of the rounded part, thus enabling easy identification of the inlet 14.

In the sensor apparatus 200, the entire area of the inner surface of the flow passage or part of the inner surface, for example, the bottom surface of the groove 15 and the wall surface of the groove 15 are hydrophilic. The flow passage having such a hydrophilic inner surface facilitates occurrence of capillary phenomenon, wherefore an analyte solution can be drawn smoothly through the inlet 14. A hydrophilic part of the inner surface of the flow passage is designed to have an angle of contact with water of less than or equal to 60°. Capillary phenomenon is caused more readily when the contact angle is less than or equal to 60°. Thus, in this case, an analyte solution can be drawn into the flow passage upon contacting the inlet more reliably.

Examples of the way that the inner surface of the groove 15 has a hydrophilic characteristic include: performing hydrophilic treatment on the inner surface of the groove 15; bonding a hydrophilic film to the inner surface of the groove 15; and using a hydrophilic material to constitute the cover member 2 in which the groove 15 is formed.

For the case with the method of performing hydrophilic treatment on the inner surface of the groove 15 and the method of bonding a hydrophilic film to the inner surface of the groove 15 in particular, an analyte solution is caused to flow along the hydrophilic part in the flow passage, wherefore most of the analyte solution flows into the flow passage. This makes it possible to restrain the analyte solution from flowing toward an unintended area, and thereby achieve measurement operation with high accuracy. Moreover, these methods allow occurrence of capillary phenomenon even in a cover member formed of a hydrophobic material, thus extending the range of choices of materials that can be used for the cover member.

For example, as the method of performing hydrophilic treatment on the inner surface of the groove 15, the inner surface of the groove 15 is subjected to oxygen-plasma ashing process to change the nature of a functional group on the surface, a silane coupling agent is applied, and polyethylene glycol is applied lastly. As an alternative, the inner surface of the groove 15 may be subjected to surface treatment using a treatment agent containing phosphoryl choline.

Figure 19:
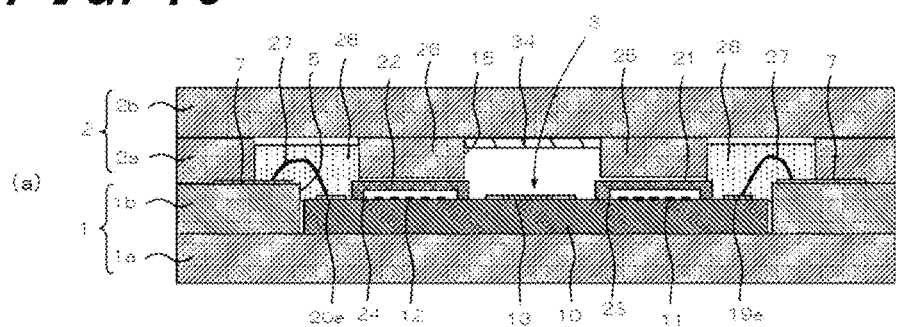
FIGS. 19(a)-19(c) illustrate sectional views showing a sensor apparatus in which a hydrophilic film is fitted to a flow passage, in accordance with some embodiments of the invention.
Figure 19:
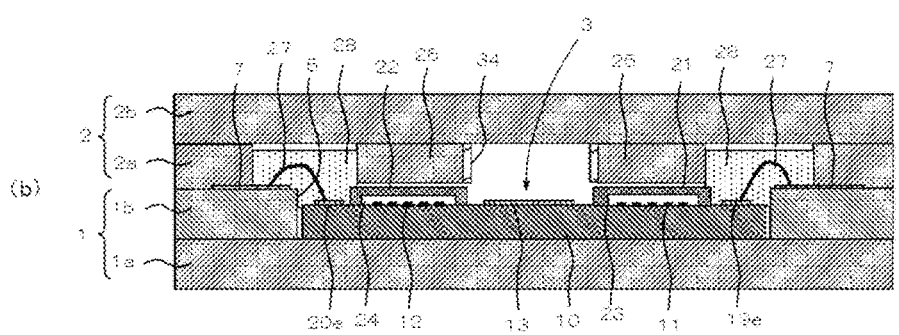
Figure 19:
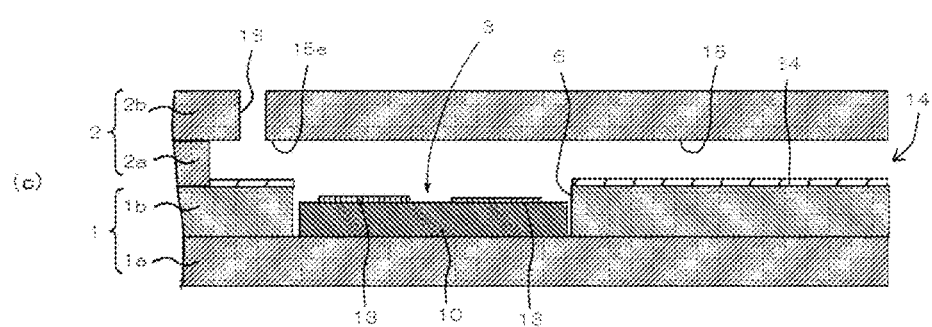

Moreover, in the method of bonding a hydrophilic film, for example, a commercially available polyester film, polyethylene film or the like having undergone the hydrophilic treatment may be used. In FIG. 19, there is shown a case where a hydrophilic film 34 adheres to the flow passage. FIG. 19(a) and FIG. 19(b) are sectional views corresponding to FIG. 14(a), and FIG. 19(c) is a sectional view corresponding to FIG. 14(b). As shown in FIG. 19(a), the film 34 may be formed only on the upper surface of the flow passage, namely the bottom surface of the groove 15. Or, as shown in FIG. 19(b), the film 34 may be formed only on the periphery of the flow passage, namely the inner wall of the groove 15. Alternatively, as shown in FIG. 19(c), the film 34 may also be formed on the lower surface of the flow passage. Moreover, the forms exemplified in FIG. 19(a) to FIG. 19(c) may be used in combination.

While the flow passage for an analyte solution constituted by the groove 15 has a depth of about 0.3 mm, the detection element 3 has a thickness of about 0.3 mm, that is; the depth of the flow passage and the thickness of the detection element 3 are substantially equal to each other. Therefore, the flow passage becomes blocked by the detection element 3 located on it. In this regard, in the sensor apparatus 200, as shown in FIG. 14, the element storage recess 5 is formed in the first cover member 1 on which the detection element 3 is mounted. The detection element 3 is stored in this element storage recess 5 to avoid blocking of the flow passage for an analyte solution. That is, the depth of the element storage recess 5 is adjusted to be substantially equal to the thickness of the detection element 3 to allow the detection element 3 to be mounted in the element storage recess 5, thus providing the flow passage constituted by the groove 15.

Figure 13:
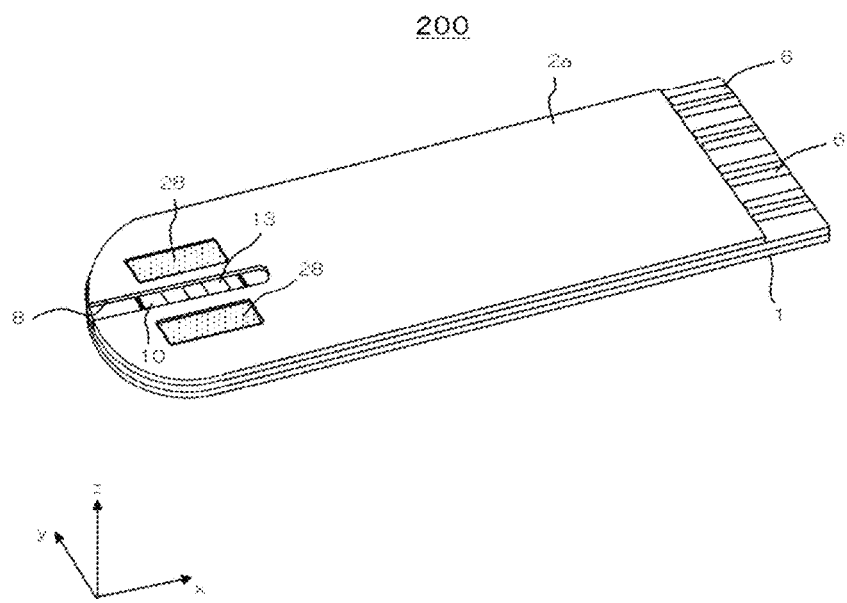
FIG. 13 is a perspective view showing the sensor apparatus shown in FIG. 11, with a fourth substrate removed, in accordance with one embodiment of the invention.

FIG. 13 is a perspective view showing the second cover member 2, with the fourth substrate 2b removed. With the provision of the flow passage for an analyte solution, an analyte solution which has flowed into the flow passage under capillary phenomenon can be guided smoothly to the detection portion 13.

From the viewpoint of attaining an adequate flow passage for an analyte solution, as shown in FIG. 14, it is advisable to adjust the distance (height) between the upper surface of the element substrate 10 and the bottom surface of the element storage recess 5 to be substantially equal to or smaller (lower) than the depth of the element storage recess 5. For example, in a case where the height of the element substrate 10 above the bottom surface of the element storage recess 5 is equal to the depth of the element storage recess 5, looking down from the inlet 14 at the inside of the groove 15, the bottom surface of the flow passage and the detection portion 13 stand at substantially the same level. In the sensor apparatus 200, the thickness of the element substrate 10 is smaller than the depth of the element storage recess 5, and, the distance (height) between the upper surface of each of the first and second protective members 21 and 22 and the bottom surface of the element storage recess 5 is substantially equal to the depth of the element storage recess 5. If the height of each of the first and second protective members 21 and 22 above the bottom surface of the element storage recess 5 is greater than the depth of the element storage recess 5, the first partition portion 25 and the second partition portion 26 of the third substrate 2a need to be made thinner than other area. Adjusting the height of each of the first and second protective members 21 and 22 above the bottom surface of the element storage recess 5 to be substantially equal to the depth of the element storage recess 5 eliminates the need for such a thinning process, and thus enhances production efficiency.

For example, the element storage recess 5 is similar in planar configuration to the element substrate 10, and is yet slightly larger than the element substrate 10. More specifically, the size of the element storage recess 5 is determined so that a space which measures about 200 μm can be left between the periphery of the element substrate 10 and the inner wall of the element storage recess 5 upon placement of the element substrate 10 in the element storage recess 5.

The detection element 3 is secured to the bottom surface of the element storage recess 5 by, for example, a die-bonding material composed predominantly of resin such as epoxy resin, polyimide resin, or silicone resin. The end 19e of the first extraction electrode 19 and the wiring line 7 are electrically connected to each other by a thin metal wire 27 formed of Au, for example. The connection between the end 20e of the second extraction electrode 20 and the wiring line 7 is made in a similar way. Means for connecting the wiring line 7 with the first and second extraction electrodes 19 and 20 is not limited to the thin metal wire 27, but may be of an electrically-conductive adhesive such as a Ag paste.

There is a cavity in the part of connection between the wiring line 7 and each of the first and second extraction electrodes 19 and 20. the break of the thin metal wire 27 is suppressed when the second cover member 2 is bonded to the first cover member 1. The cavity can be created with ease by forming the first through hole 16 and the second through hole 17 in the third substrate 2a. Moreover, the first partition portion 25 lying between the first through hole 16 and the groove 15 makes it possible to restrain an analyte solution flowing through the groove 15 from flowing into the cavity defined by the first through hole 16, and thereby suppress electrical short-circuiting that is caused between a plurality of the first extraction electrodes 19 by the analyte solution. Likewise, the second partition portion 26 lying between the second through hole 17 and the groove 15 makes it possible to restrain an analyte solution flowing through the groove 15 from flowing into the cavity defined by the second through hole 17, and thereby suppress electrical short-circuiting that is caused between a plurality of the second extraction electrodes 20 by the analyte solution.

The first partition portion 25 is located above the first protective member 21, and the second partition portion 26 is located above the second protective member 22. Thus, in the stricter sense, the flow passage for an analyte solution is defined not only by the groove 15 but also by a groove-side sidewall of the first protective member 21 and a groove-side sidewall of the second protective member 22. In the interest of prevention of leakage of an analyte solution into the cavities defined by the first through hole 16 and the second through hole 17, it is preferable that the first partition portion 25 is kept in contact with the upper surface of the first protective member 21, and the second partition portion 26 is kept in contact with the upper surface of the second protective member 22. However, in the sensor apparatus 200, a space is left between the lower surface of the first partition portion 25 and the upper surface of the first protective member 21, as well as between the lower surface of the second partition portion 26 and the upper surface of the second protective member 22. The space measures in the range of, for example, 10 μm to 60 μm. For example, when the sensor apparatus 200 is taken with fingers, a pressure is applied to the part contacting the fingers. At this time, with such a space, the pressure can be absorbed by the space, thus suppressing application of the pressure directly to the first and second protective members 21 and 22. This helps restrain the first vibration space 23 and the second vibration space 24 from becoming deformed greatly. Moreover, since an analyte solution generally exhibits a certain degree of viscoelasticity, by providing a space which measures in the range of 10 μm to 60 μm, the analyte solution is not allowed to find its way into the space easily, thus suppressing leakage of the analyte solution into the cavities defined by the first through hole 16 and the second through hole 17.

The first partition portion 25 is greater in width than the first vibration space 23. In other words, the sidewall of the first partition portion 25 is located above the frame body of the first protective member 21. In this case, even if the first partition portion 25 is brought into contact with the first protective member 21 under an external pressure, the first partition portion 25 can be supported by the frame body, thus suppressing deformation of the first protective member 21. By the same token, the width of the second partition portion 26 is preferably made greater than the width of the first vibration space 25.

The first extraction electrode 19, the second extraction electrode 20, the thin metal wire 27, and the wiring line 7 located inside the cavities defined by the first through hole 16 and the second through hole 17 are covered with an insulating member 28. Covering the first extraction electrode 19, the second extraction electrode 20, the thin metal wire 27, and the wiring line 7 with the insulating member 28 helps retard corrosion of these components. Moreover, with the insulating member 28, even if an analyte solution finds its way into the space between the first partition portion 25 and the first protective member 21, or the space between the second partition portion 26 and the second protective member 22, the flow of the analyte solution is stemmed by the insulating member 28. This helps suppress electrical short-circuiting that is caused, for example, between the extraction electrodes by the leakage of the analyte solution.

Thus, according to the sensor apparatus 200, since the detection element 3 is stored in the element storage recess 5 of the first cover member 1, it is possible to attain the flow passage for an analyte solution extending from the inlet 14 to the detection portion 13, and thereby cause an analyte solution drawn into the flow passage through the inlet under capillary phenomenon or otherwise to flow to the detection portion 13. That is, there is provided the sensor apparatus 200 that incorporates the detection element 3 having a certain thickness and yet includes, in itself, the analyte suction mechanism.

Next, modified examples of the sensor apparatus 200 of the second embodiment will be described.

Modified Example

Figure 17:
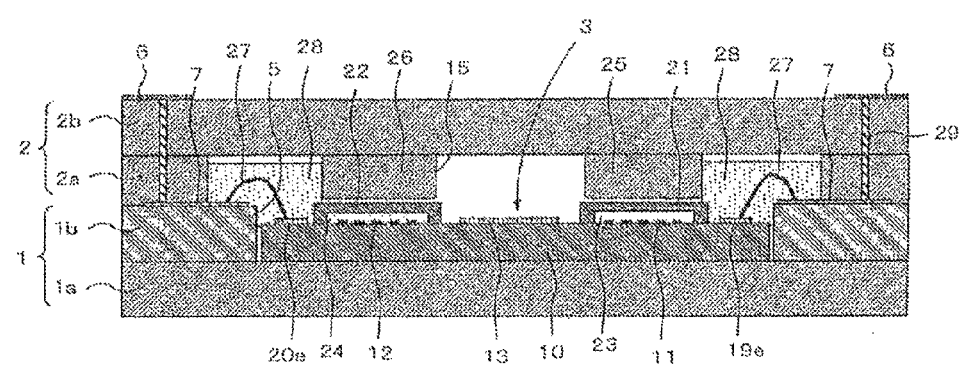
FIG. 17 is a sectional view showing a modified example of the sensor apparatus of FIG. 11, in accordance with one embodiment of the invention.

FIG. 17 is a sectional view showing a sensor apparatus 201 which is a modified example of the sensor apparatus 200 shown in FIG. 11. This sectional view corresponds to the sectional view shown in FIG. 14(a).

This modified example differs from the afore-stated sensor apparatus 200 in a position for forming the terminal 6. In contrast to the above-mentioned embodiment in which, as shown in FIG. 11, the terminal 6 is formed at the other end of the second substrate 1b in the longitudinal direction, in this modified example, as shown in FIG. 17, the terminal 6 is formed on the upper surface of the fourth substrate 2b. As shown in FIG. 17, the terminal 6 and the wiring line 7 are electrically connected to each other by a through conductor 29 passing through the second cover member 2. For example, the through conductor 29 is formed of an Ag paste or formed by plating.

As an alternative to the modified example, the terminal 6 may be formed on the lower surface of the first cover member 1.

Thus, the terminal 6 may be formed in any location on the surfaces of the first cover member 1 and the second cover member 2, and its position is determined in accordance with the type of measuring equipment in use.

Figure 18:
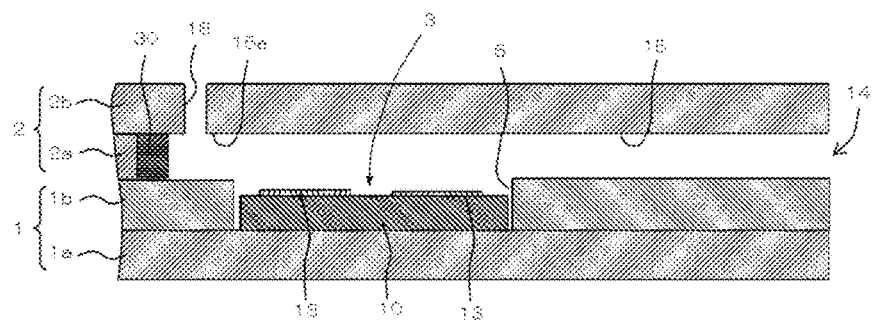
FIG. 18 is a sectional view showing a modified example of the sensor apparatus of FIG. 11, in accordance with one embodiment of the invention.

FIG. 18 is a sectional view showing a sensor apparatus 202 which is a modified example of the sensor apparatus 200 shown in FIG. 11. This sectional view corresponds to the sectional view shown in FIG. 14(b).

In this modified example, a liquid absorbing member 30 which absorbs an analyte solution at a predetermined absorption rate is disposed at the far end of the flow passage defined by the groove 15.

This permits absorption of an excess of an analyte solution, renders the amount of an analyte solution flowing over the detection portion 13 uniform throughout the detection portion 13, and achieves measurement operation with stability. For example, a porous material, such as a sponge, capable of liquid absorption can be used for the liquid absorbing member 30.

Third Embodiment

Figure 20:
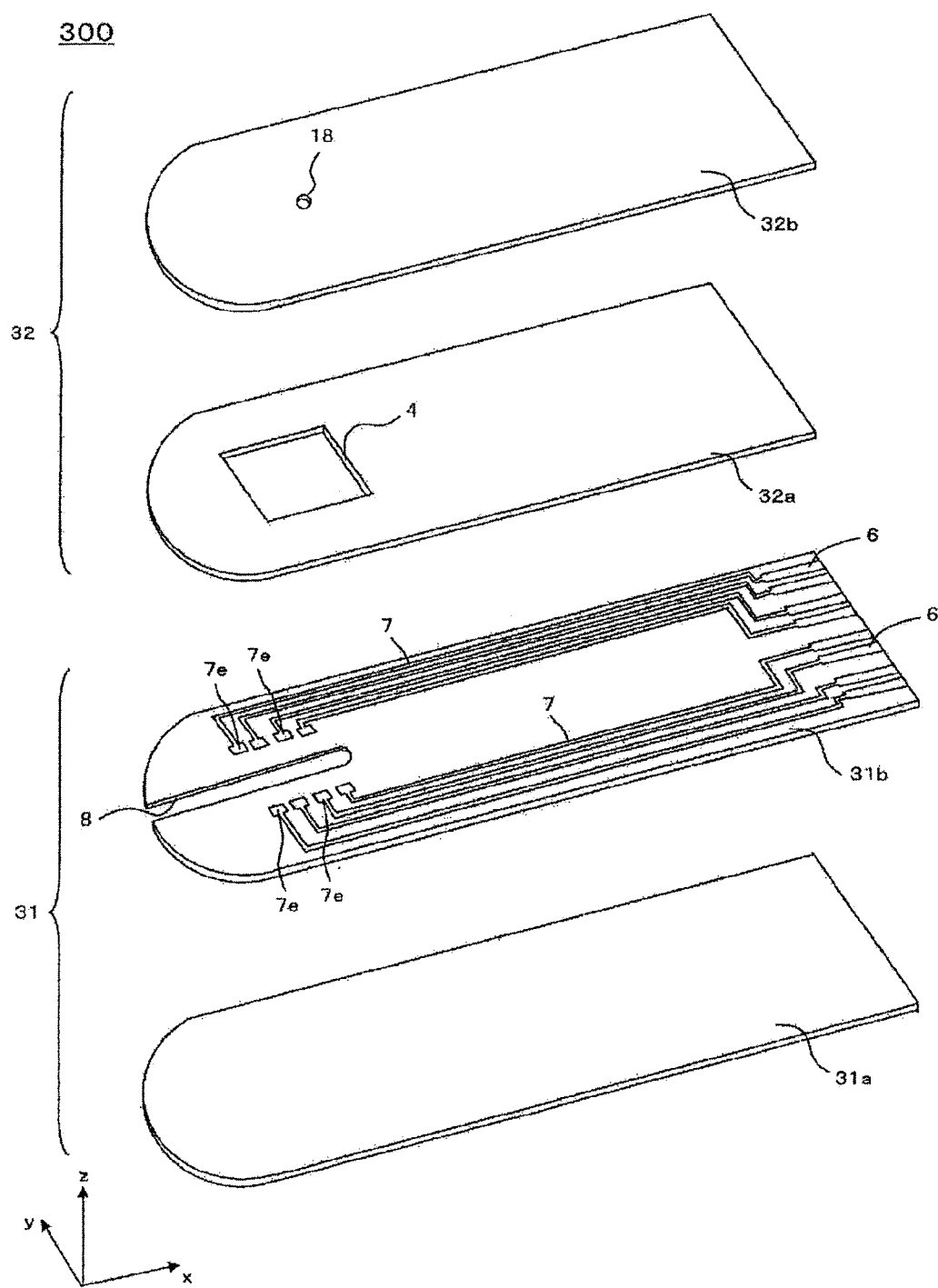
FIG. 20 is an exploded perspective view of a mounting member and a cover member used in a sensor apparatus in accordance with a third embodiment of the invention.
Figure 21:
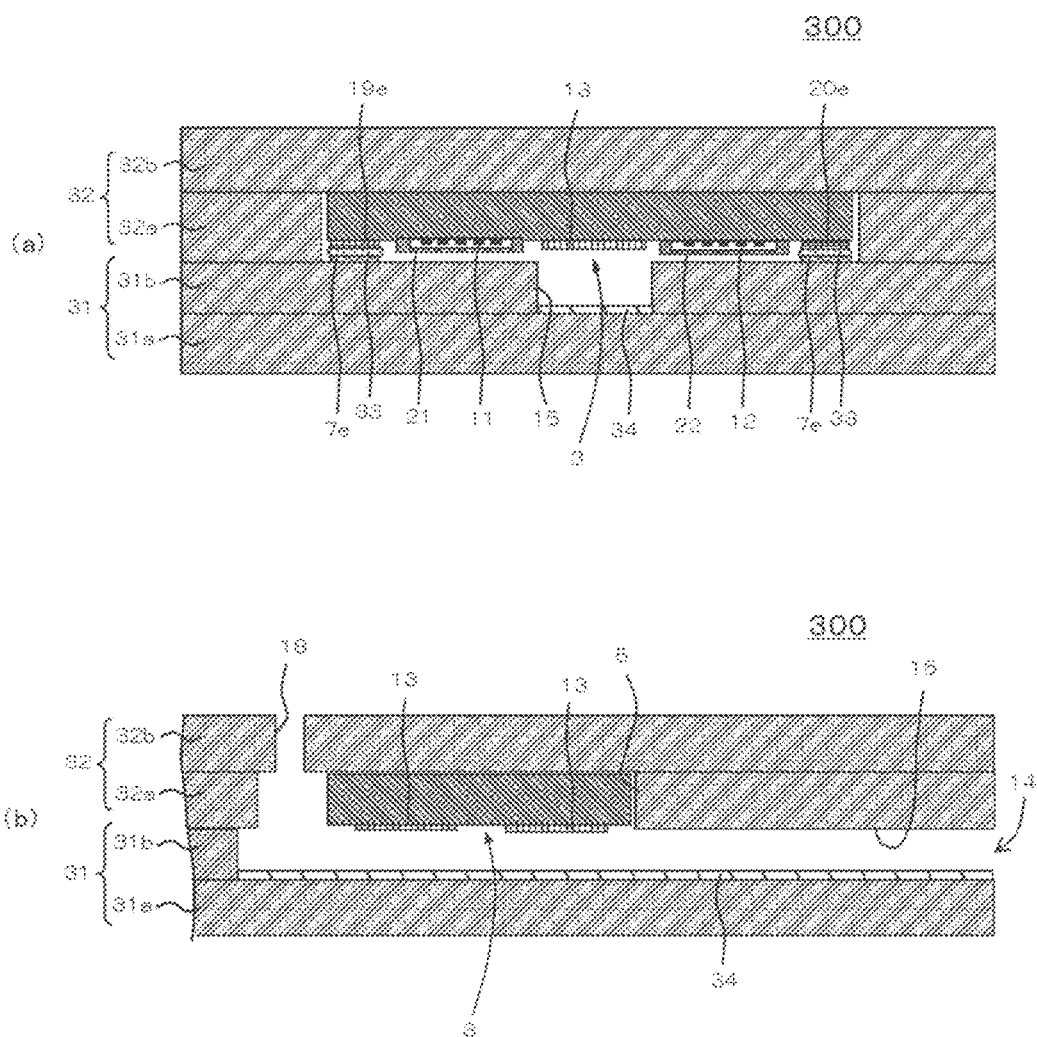
FIG. 21(a) is a sectional view corresponding to FIG. 14(a), in accordance with one embodiment of the invention.
FIG. 21(b) is a sectional view corresponding to FIG. 14(b), in accordance with one embodiment of the invention.

Next, a sensor apparatus 300 in accordance with a third embodiment of the invention will be described with reference to FIG. 20 and FIG. 21. FIG. 20 is an exploded perspective view of a mounting member 31 and a cover member 32 used in the sensor apparatus 300, and FIG. 21 is a sectional view, and more specifically FIG. 21(a) and FIG. 21(b) are sectional views that correspond to FIG. 14(a) and FIG. 14(b), respectively.

Major differences of the sensor apparatus 300 from the afore-stated sensor apparatus 200 of the second embodiment are the shape of the cover member and the way of mounting the detection element 3.

Specifically, in contrast to the sensor apparatus 200 of the second embodiment in which the detection element 3 is mounted so that the surface formed with the detection portion 13 and the first and second IDT electrodes 11 and 12 faces upward (the z direction), and the lower surface of the element substrate 3 is fitted to the first cover member 1, in the sensor apparatus 300, the detection element 3 is mounted to the mounting member 31 so that the surface formed with the detection portion 13 and the first and second IDT electrodes 11 and 12 faces downward (the −z direction). That is, in the sensor apparatus 300, the detection element 3 is face-down mounted.

As an example of the way of face-down mounting the detection element 3, the end 19e of the first extraction electrode 19 formed on the element substrate 3 and an end 7e of the wiring line 7 formed on the mounting member 31 are joined to each other by an electrically-conductive joining material 33 such as solder, and, likewise, the end 20e of the second extraction electrode 20 formed on the element substrate 3 and the end 7e of the wiring line 7 formed on the mounting member 31 are joined to each other by an electrically-conductive joining material 33 such as solder. As an alternative to this joining method using solder, for example, a joining method using an electrically-conductive bump of Au or the like may be adopted.

In the case of face-up mounting the detection element 3 as in the sensor apparatus 200 of the second embodiment, a mechanical connection between the detection element 3 and the first cover member 1 is made by a die-bonding material interposed between the lower surface of the element substrate 3 and the bottom surface of the element storage recess of the first cover member 1, and, an electrical connection between the element substrate 3 and the first cover member 1 is made by the thin metal wire 27. That is, the mechanical connection and the electrical connection are established independently.

On the other hand, in the case of face-down mounting the detection element 3 as in the sensor apparatus 300, the detection element 3 and the mounting member 31 can be connected both mechanically and electrically to each other at one time, thus enhancing production efficiency.

Moreover, the sensor apparatus 300 differs from the sensor apparatus 200 of the second embodiment also in the shape of the cover member. In the sensor apparatus 200 of the second embodiment, of the first and second cover members 1 and 2 that are lower and upper cover members, respectively, the lower first cover member 1 is provided with the element storage recess 5, and, the detection element 3 is stored in this element storage recess 5 so that the flow passage is extended to the detection portion 13 without being blocked by the detection element 3. On the other hand, in the sensor apparatus 300, as shown in FIG. 21, of the mounting member 31 and the cover member 32 that are lower and upper members, respectively, the upper cover member 1 has the element storage recess 5 in a lower surface thereof, and, the detection element 3 is stored in this element storage recess 5. This makes it possible to store the detection element 3 having a certain thickness in the cover member, as well as to attain a flow passage extended to a region located below the detection portion 13.

As shown in FIG. 20, the mounting member 31 is composed of a fifth substrate 31a and a sixth substrate 31b, and, the cover member 32 is composed of a seventh substrate 32a and an eighth substrate 32b.

The fifth substrate 31a in the form of a flat plate is basically identical with the first substrate 1a of the second embodiment. Meanwhile, the sixth substrate 31b bonded to the fifth substrate 31b differs from the second substrate 1b of the second embodiment in that it is formed with a cutaway 8. The sixth substrate 31b having the cutaway 8 is laminated on the flat plate-shaped fifth substrate 31a, thus constituting a fifth cover member 31 which has an inlet at one end, and also has a groove 15 extending from the inlet.

Of the seventh substrate 32a and the eighth substrate 32b constituting the cover member 32, the lower seventh substrate 32a is formed with a recess-forming through hole 4. The flat plate-shaped eighth substrate 32b is laminated on the seventh substrate 32 having the recess-forming through hole 4, thus constituting the cover member 32 having the element storage recess 5 in a lower surface thereof. The eighth substrate 32b is basically identical with the fourth substrate 2b of the second embodiment.

Moreover, in the sensor apparatus 300, as shown in FIG. 21, a hydrophilic film 34 is formed on the bottom surface of a groove 5. Meanwhile, the sixth substrate 31 is formed of a hydrophobic material. In this case, an analyte solution basically flows into the flow passage defined by the groove 5, and is thus restrained from finding its way into a space between the first protective member 21 and the upper surface of the sixth substrate 31 and a space between the second protective member 22 and the upper surface of the sixth substrate 31. This helps suppress electrical short-circuiting that is caused, for example, between the ends 19e of, respectively, the first extraction electrodes 19 by the analyte solution.

Fourth Embodiment

Next, a sensor apparatus 400 in accordance with a fourth embodiment of the invention will be described with reference to FIG. 22 to FIG. 25.

Major differences of the sensor apparatus 400 from the afore-stated sensor apparatus 200 of the second embodiment are placement of an auxiliary substrate 35 and the configuration of a part of the detection element 3 in which the first vibration space 23 and the second vibration space 24 are formed.

Figure 22:
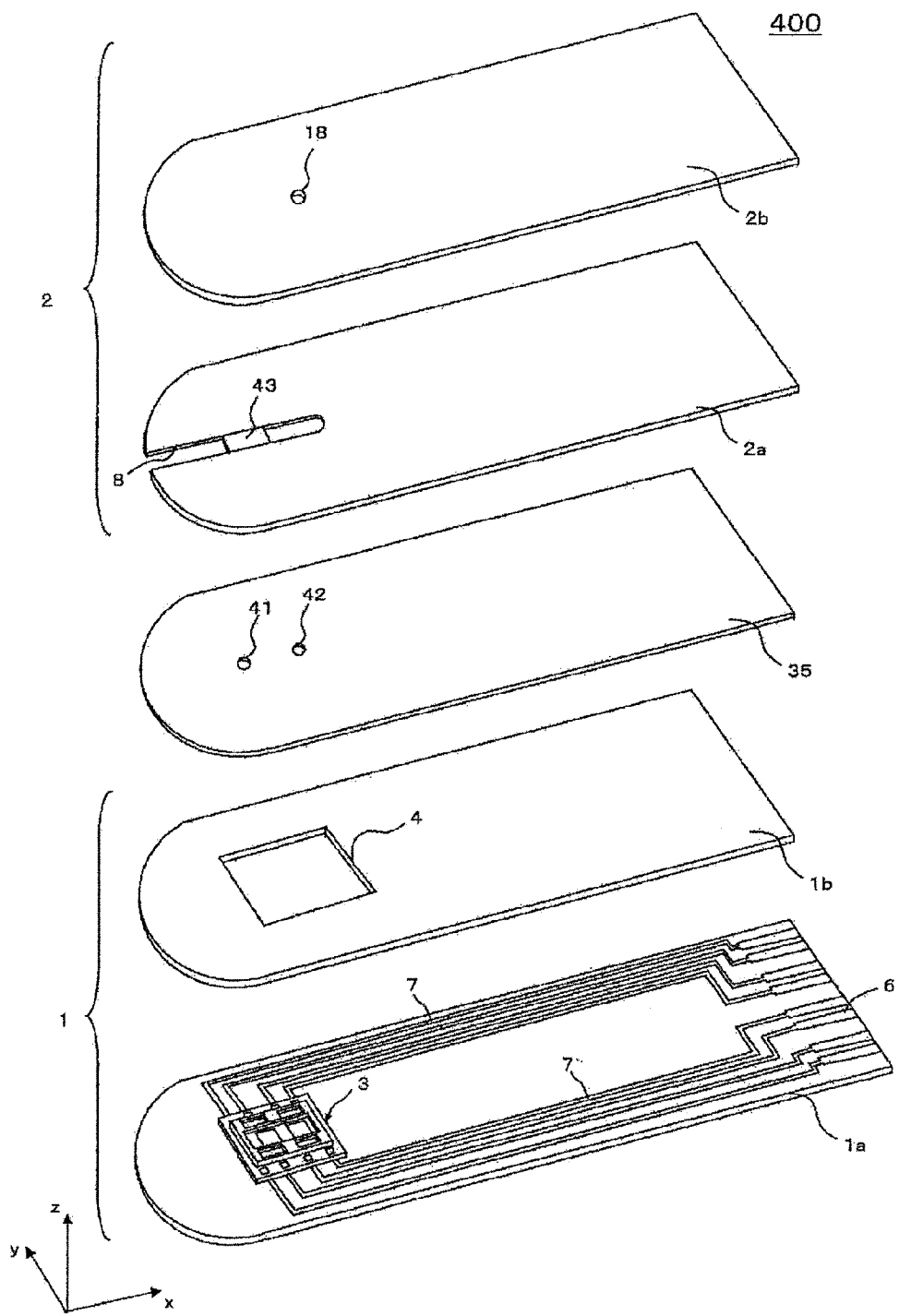
FIG. 22 is an exploded perspective view of a sensor apparatus in accordance with a fourth embodiment of the invention.

As shown in FIG. 22, the auxiliary substrate 35 is a substrate interposed between the first cover member 1 and the second cover member 2, which is identical in outer shape and size with the second substrate 1b, for example. Moreover, the auxiliary substrate 35 has a thickness of 0.1 mm to 0.5 mm, for example. The auxiliary substrate 35 is bonded to a second substrate 1b located there below and a third substrate 2a located there above by an adhesive or a double-faced tape, for example.

As stated in the description of the second embodiment, the element storage recess 5 for storing the detection element 3 is slightly greater in planar configuration than the detection element 3. Thus, a space is left between the periphery of the detection element 3 and the inner wall of the element storage recess 5. The auxiliary substrate 35 acts to close this space. Moreover, the auxiliary substrate 35 constitutes a part of a flow passage located above the detection element 3.

Figure 23:
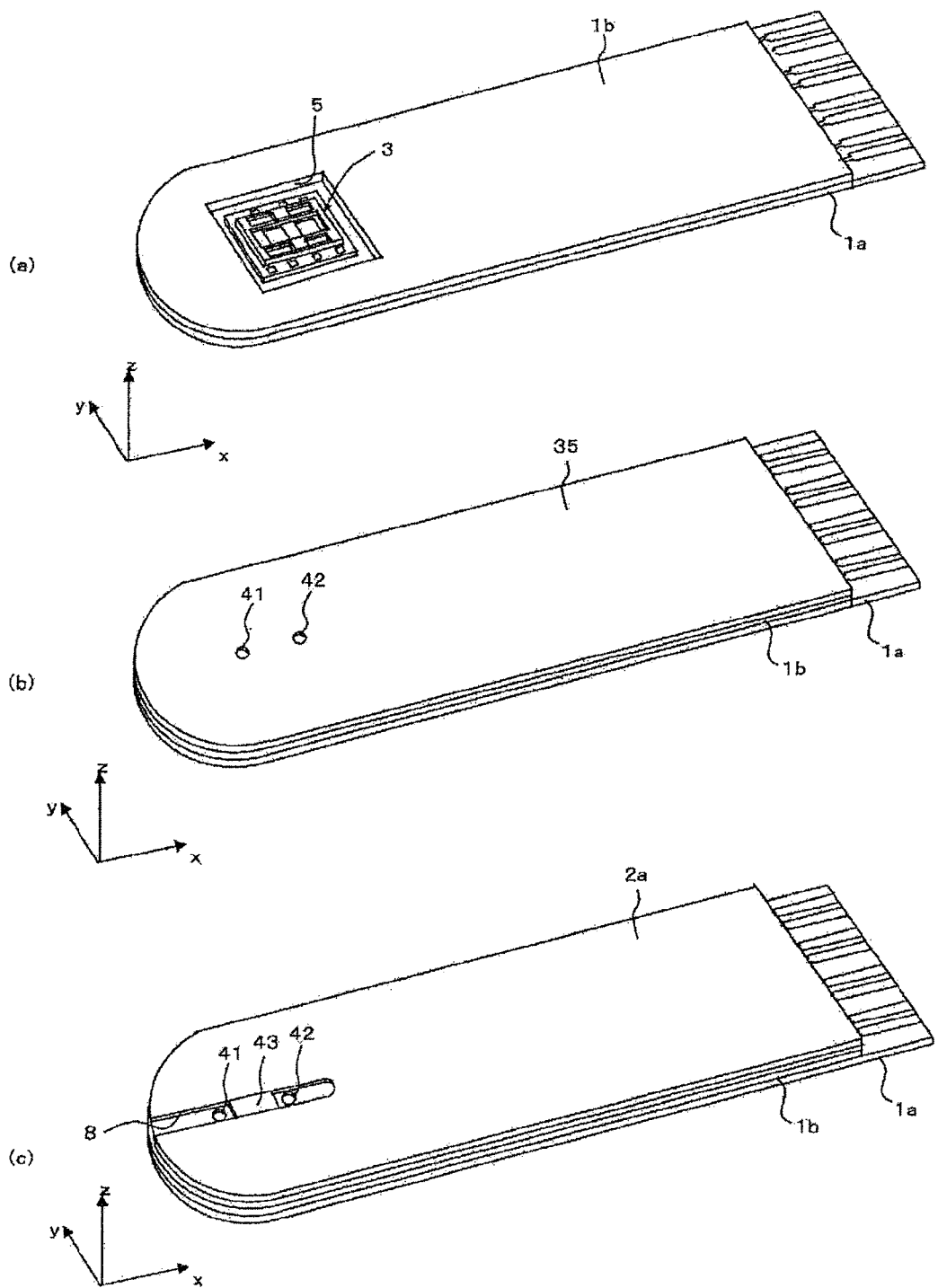
FIG. 23(a) is a perspective view of the sensor apparatus shown in FIG. 22, with a second cover member and an auxiliary substrate removed.
FIG. 23(b) is a perspective view of the sensor apparatus shown in FIG. 22, with the second cover member removed.
FIG. 23(c) is a perspective view of the sensor apparatus shown in FIG. 22, with a fourth substrate removed.
Figure 24:
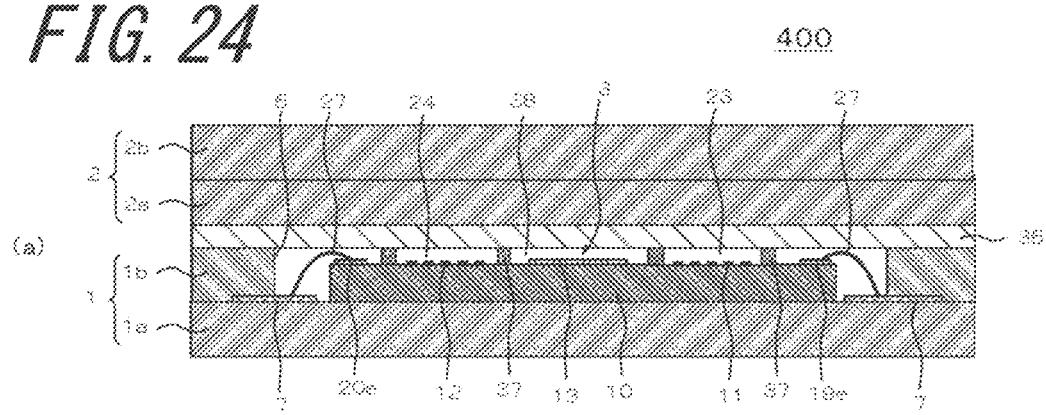
FIG. 24(a) is a sectional view of the sensor apparatus shown in FIG. 17 and a part corresponding to FIG. 14(a)
FIG. 24(b) is a sectional view of the sensor apparatus shown in FIG. 17 and a part corresponding to FIG. 14(b)
Figure 24:
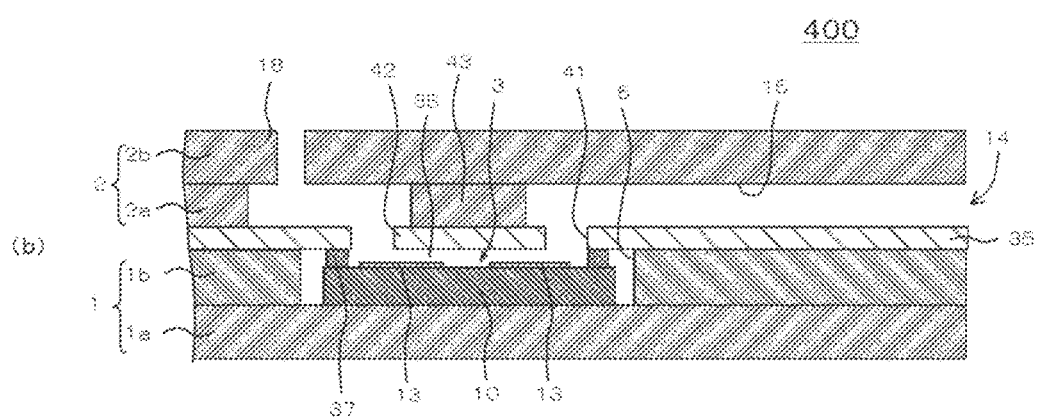

Referring to FIG. 23 and FIG. 24, there is described how the auxiliary substrate 35 closes the space between the periphery of the detection element 3 and the inner wall of the element storage recess 5 while constituting the flow passage. FIG. 23(a) to FIG. 23(c) are perspective views of the sensor apparatus 400, with predetermined constituent components removed. Specifically, FIG. 23(a) is a perspective view, with the second cover member 2 and the auxiliary substrate 35 removed; FIG. 23(b) is a perspective view, with the second cover member 2 removed; and FIG. 23(c) is a perspective view, with the fourth substrate 2b of the second cover member 2 removed. Moreover, FIG. 24(a) is a sectional view corresponding to FIG. 14(a), and FIG. 24(b) is a sectional view corresponding to FIG. 14(b).

As shown in FIG. 23(a), with the detection element 3 stored in the element storage recess 5, a space is left between the periphery of the detection element 3 and the inner wall of the element storage recess 5. As shown in FIG. 23(b), this space is closed by the auxiliary substrate 35 laminated on the second substrate 2b.

Figure 25:
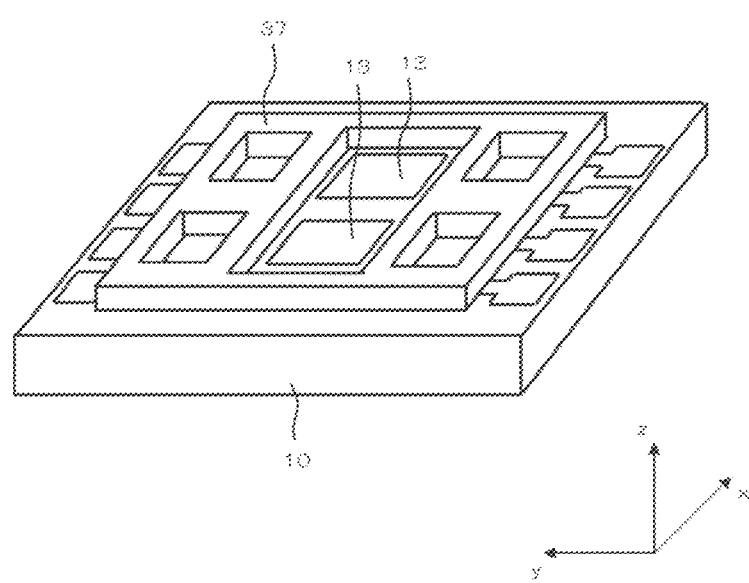
FIG. 25 is a perspective view of a detection element used in the sensor apparatus shown in FIG. 22.

Now, the structure of the detection element 3 used in the sensor apparatus 400 will be described. FIG. 25 is a perspective view of the detection element 3 used in the sensor apparatus 400. The detection element 3 includes a frame body 37 located on the upper surface of the element substrate 10. The frame body 37 has a centrally located through hole to uncover two detection portions 13, and also has a through hole to uncover each IDT electrode. That is, the frame body 37 comprises a portion for surrounding the detection portions 13 and portions for surrounding the individual IDT electrodes, respectively.

As shown in FIG. 24(a), each frame-constituting portion of the frame body 37 is closed by the auxiliary substrate 35. Thus, the auxiliary substrate 35 closes the space between the periphery of the detection element 3 and the inner wall of the element storage recess 5, and also serves as a lid for covering the frame-constituting portions of the frame body 37. The first vibration space 23 is created by closing a portion surrounding the first IDT electrode 11, and, the first IDT electrode 11 is hermetically sealed in the first vibration space 23. Likewise, the second vibration space 24 is created by closing a portion surrounding the second IDT electrode 12, and, the second IDT electrode 12 is hermetically sealed in the second vibration space 24. Moreover, a portion surrounding the detection portions 13 is also closed, thus creating a space 38 there.

The upper surface of the frame body 37 and the upper surface of the second substrate 1b are positioned at the same level. In other words, the thickness of the frame body 37 is equivalent to a difference between the thickness of the second substrate 1b and the thickness of the element substrate 10. The placement of the frame body 37 having such a thickness makes it possible to close the space between the periphery of the detection element 3 and the inner wall of the element storage recess 5, as well as to close the frame-constituting portions of the frame body 37. The thickness of the frame body 37 is set at 50 μm, for example.

Returning to FIG. 23(b), the auxiliary substrate 35 is formed with a first hole portion 41 and a second hole portion 42. The first hole portion 41 and the second hole portion 42 are each communicated with the interior of the portion of the frame body 37 surrounding the detection portions 13.

The third substrate 2a having a cutaway 8 is laminated on the upper surface of the auxiliary substrate 35 having the first hole portion 41 and the second hole portion 42. The first hole portion 41 and the second hole portion 42 are formed so as to be located in overlapping relation with the cutaway 8 when the third substrate 2a is located on the auxiliary substrate 35. Since the cutaway 8 constitutes the groove 15, it follows that the groove 15 and the space 38 are communicated with each other via the first and second hole portions 41 and 42. The first hole portion 41 is located toward an opened end of the cutaway 8 serving as an inlet for inflow of an analyte solution, whereas the second hole portion 42 is spaced away from the opened end of the cutaway 8 beyond the first hole portion 41. Moreover, a partition wall 43 is formed in a part of the cutaway 8 which lies between the first hole portion 41 and the second hole portion 42. The first hole portion 41 and the second hole portion 42 may be given any planar configuration, for example, a circular shape or a rectangular shape, and may either be identical with or different from each other in shape and size.

A flow passage for an analyte solution in the thereby constructed sensor apparatus 400 will be described with reference to a sectional view shown in FIG. 24. As stated in the description of the second embodiment, upon contacting the inlet 14, an analyte solution flows into the flow passage defined by the groove 15 under capillary phenomenon. After reaching the first hole portion 41, the flowing analyte solution finds its way into the space 38 through the first hole portion 41 under capillary phenomenon, thus filling the space 38 with the analyte solution. At this time, air present in the space 38 is expelled through the second hole portion 42. Under this condition, a measurement of the analyte solution is conducted. Thus, in the sensor apparatus 400, the space 38 constitutes a part of the flow passage. At least the surface of the auxiliary substrate 35 has a hydrophilic property to expedite the occurrence of capillary phenomenon. Moreover, With the partition wall 43, when an analyte solution reaches there, the flow of the analyte solution is stemmed by the partition wall 43, thus causing the analyte solution to find its way into the space 38.

As shown in FIG. 24(a), the frame body 37 and the auxiliary substrate 35 serve to separate the space 38 and the first and second vibration spaces 23 and 24, thus restraining an analyte solution which has flowed into the space 38 from flowing into the first and second vibration spaces 23 and 24. Moreover, the space between the periphery of the detection element 3 and the inner wall of the element storage recess 5 is closed by the auxiliary substrate 35, wherefore the analyte solution is not allowed to flow into the space.

Accordingly, the sensor apparatus 400 is capable of restraining an analyte solution from flowing into an unwanted area, and thus suppressing electrical short-circuiting that is caused between the individual wiring lines. Moreover, the amount of an analyte solution flowing through the flow passage can be rendered uniform.

Moreover, in contrast to the above-mentioned embodiment, in the sensor apparatus 400, the wiring line 7 is disposed on the first substrate 1a which is the lowermost layer. In this case, the thin metal wire 27, which provides connection between the wiring line 7 and each of the ends 19e and 20e of, respectively, the first and second extraction electrodes of the detection element 3, is run downward from the upper surface of the detection element 3, wherefore the level of a curved part of the thin metal wire 27 is not so high. This makes it possible to render the crest of the curved part of the thin metal wire 27 lower than the height of the frame body 37 with ease, and thereby eliminate the need for extra process to avoid a contact of the thin metal wire 27 with the auxiliary substrate 35, thus enhancing production efficiency. Note that the position of placement of the wiring line 7 is not limited to this, and thus, as with the second embodiment, the wiring line 7 may be disposed on the second substrate 1b. For a case where the thin metal wire 27 is brought into contact with the auxiliary substrate 35 during bonding operation, it is advisable to increase the thickness of the frame body 37 or create a through hole in a part of the auxiliary substrate 35 which is located immediately above the thin metal wire 27.

Next, a modified example of the sensor apparatus 400 of the fourth embodiment will be described.

Modified Example

Figure 26:
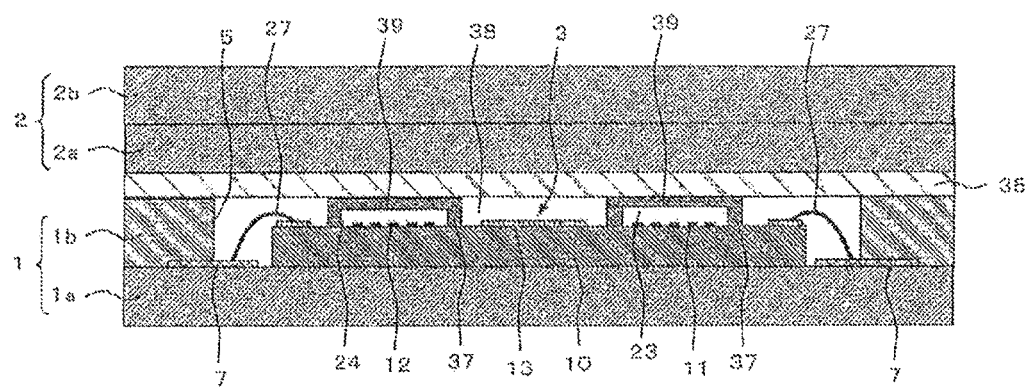
FIG. 26 is a sectional view showing a modified example of the sensor apparatus shown in FIG. 22.

FIG. 26 is a view showing a sensor apparatus 401 which is a modified example of the sensor apparatus 400 shown in FIG. 22. This view is a sectional view corresponding to FIG. 24(a).

In contrast to the afore-stated sensor apparatus 400 in which, as shown in FIG. 24(a), the auxiliary substrate 35 serves also as a lid for the frame body 37, in this modified example, as shown in FIG. 26, a second frame body 37b is provided independently of the auxiliary substrate 35.

Figure 27:
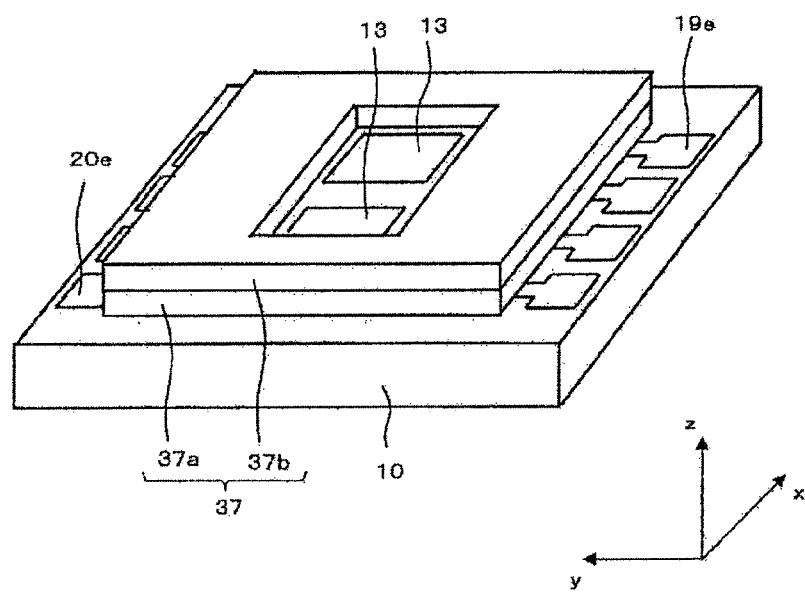
FIG. 27 is a perspective view of a detection element used in the sensor apparatus shown in FIG. 26.

FIG. 27 is a perspective view of a detection element 3 used in the sensor apparatus 401 according to this modified example. The detection element 3 of this modified example differs from the detection element 3 shown in FIG. 25 in the structure of the frame body 37.

As shown in FIG. 27, the frame body 37 of this modified example has a double-layer form consisting of a first frame body 37a and a second frame body 37b laminated on the first frame body 37a. The first frame body 37a is constructed identically with the frame body 37 of the sensor apparatus 400, and thus comprises a portion for surrounding two detection portions 13 and portions for surrounding individual IDT electrodes, respectively. The second frame body 37b, while being identical with the first frame body 37a in outer shape and size as seen in a plan view, has no through holes in positions corresponding to the positions of the first IDT electrode 11 and the second IDT electrode 12, respectively. Thus, the portion surrounding the first IDT electrode 11 is closed by the second frame body 37b, thus creating a first vibration space 23, and likewise, the portion surrounding the second IDT electrode 12 is closed by the second frame body 37b, thus creating a second vibration space 24.

Meanwhile, the second frame body 37b has, in an area immediately above the detection portions 13, a through hole which is identical in shape and size with the through hole of the first frame body 37a, and this area is closed by the auxiliary substrate 35, thus creating the space 38 constitutes a part of the flow passage.

The placement of the frame body 37 having such a structure makes it possible to increase the area of contact between the auxiliary substrate 35 and the frame body 37, and thereby adhere the auxiliary substrate 35 to a lid body 39 firmly.

Fifth Embodiment

Next, a sensor apparatus 500 in accordance with a fifth embodiment of the invention will be described with reference to FIG. 28 to FIG. 30.

A major difference of the sensor apparatus 500 from the afore-stated sensor apparatus 200 of the second embodiment is placement of an auxiliary substrate 44.

Figure 28:
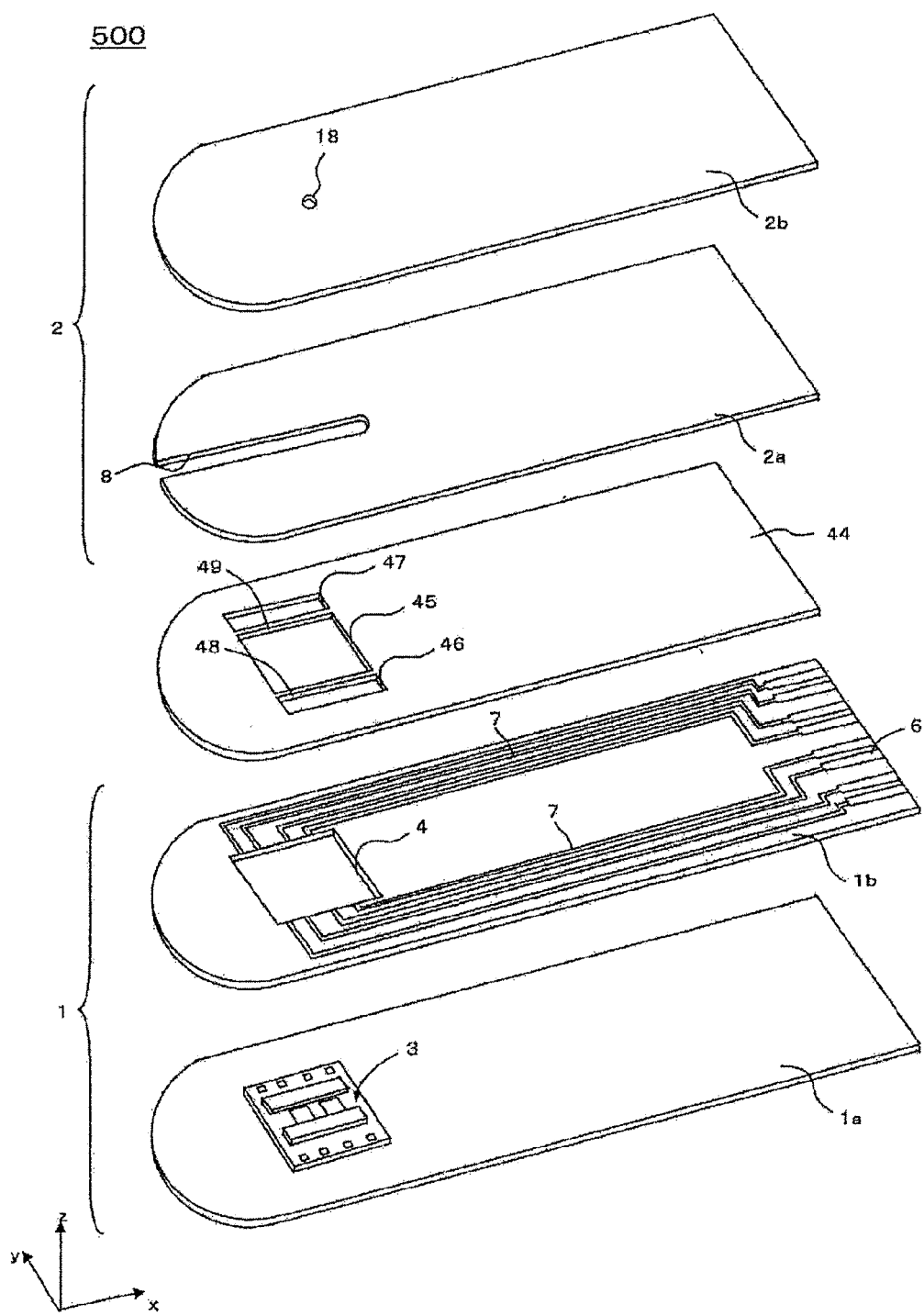
FIG. 28 is an exploded perspective view of a sensor apparatus in accordance with a fifth embodiment of the invention.
Figure 29:
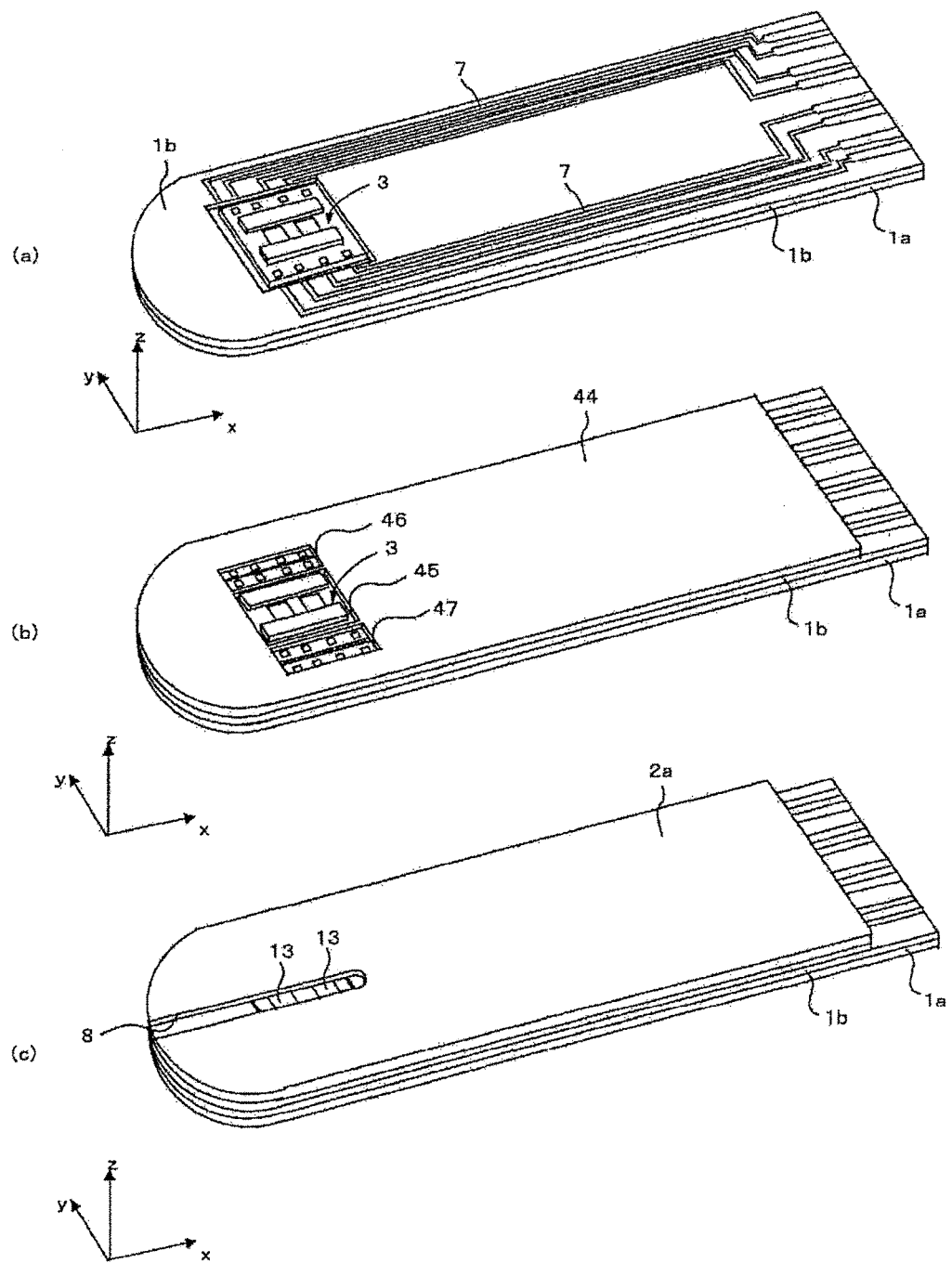
FIG. 29(a) is a perspective view of the sensor apparatus shown in FIG. 28, with a second cover member and an auxiliary substrate removed.
FIG. 29(b) is a perspective view of the sensor apparatus shown in FIG. 28, with the second cover member removed.
FIG. 29(c) is a perspective view of the sensor apparatus shown in FIG. 28, with a third substrate removed.

As shown in FIG. 28, the auxiliary substrate 44 is a substrate in flat-plate form that is interposed between the first cover member 1 and the second cover member 2. The auxiliary substrate 44 is identical in outer shape and size with the third substrate 2a. Moreover, the auxiliary substrate 35 has a thickness of 0.1 mm to 0.5 mm, for example. The auxiliary substrate 44 is bonded to a second substrate 1b located there below and the third substrate 2a located there above by an adhesive or a double-faced tape, for example. The auxiliary substrate 44 is formed with a hole portion 45 to uncover the detection portion 13 of the detection element 3 when the auxiliary substrate 44 overlies the first cover member 1. As will hereafter be described, on both sides of the hole portion 45, there are provided a third hole portion 45 and a fourth through hole 46 that function similarly to the first and second through holes 16 and 17 formed in the third substrate 2a of the sensor apparatus 200 of the second embodiment.

The auxiliary substrate 44 acts to separate a flow passage for an analyte solution and a space left between the periphery of the detection element 3 and the inner wall of the element storage recess 5. This will be described with reference to FIG. 29 and FIG. 30. FIG. 29(a) to FIG. 29(c) are perspective views of the sensor apparatus 500, with predetermined constituent components removed. Specifically, FIG. 29(a) is a perspective view, with the second cover member 2 and the auxiliary substrate 44 removed; FIG. 29(b) is a perspective view, with the second cover member 2 removed; and FIG. 29(c) is a perspective view, with the fourth substrate 2b of the second cover member 2 removed. Moreover, FIG. 30(a) is a sectional view corresponding to FIG. 14(a), and FIG. 30(b) is a sectional view corresponding to FIG. 14(b).

As shown in FIG. 29(a), with the detection element 3 stored in the element storage recess 5, a space is left between the periphery of the detection element 3 and the inner wall of the element storage recess 5. Upon placement of the auxiliary substrate 44, as shown in FIG. 29(b), the hole portion 45 formed in the auxiliary substrate 44 uncovers a part of the detection element 3. The size of the hole portion 45 is determined so that the outer edge of the hole portion 45 is located inwardly of the outer edge of the detection element 3. Thus, in the sensor apparatus 500, of the space created between the periphery of the detection element 3 and the inner wall of the element storage recess 5, a space located at either end in the x direction (a space extending along the y direction) lies under the auxiliary substrate 44.

That is, of the space created between the periphery of the detection element 3 and the inner wall of the element storage recess 5, a space located at either end in the x direction is closed by the auxiliary substrate 44. On the other hand, of the space created between the periphery of the detection element 3 and the inner wall of the element storage recess 5, a space located at either end in the y direction (a space extending along the x direction) is left exposed from the third through hole 46 and the fourth through hole 47.

The third substrate 2a having a cutaway 8 is laminated on the upper surface of the auxiliary substrate 44 laminated on the first cover member 1. Since the auxiliary substrate 44 has the hole portion 45 to uncover the detection portion 13, in a condition as shown in FIG. 29(c), the detection portion 13 is left exposed from the cutaway 8 as seen in a plan view.

Figure 30:
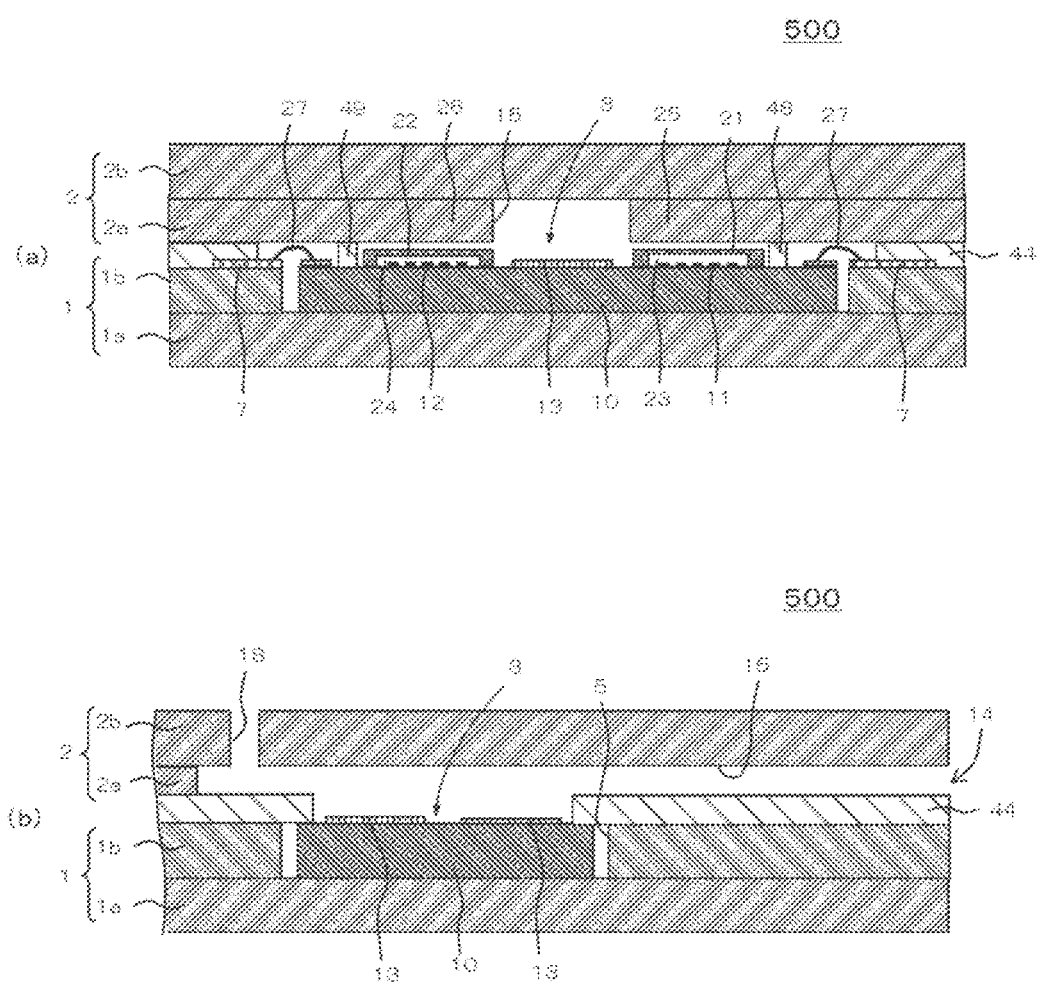
FIG. 30(a) is a sectional view of the sensor apparatus shown in FIG. 28 and a part corresponding to FIG. 14(a)
FIG. 30(b) is a sectional view of the sensor apparatus shown in FIG. 28 and a part corresponding to FIG. 14(b).

As shown in a sectional view of FIG. 30, the flow passage for an analyte solution of the sensor apparatus 500 comprising such a construction is basically the same as that of the sensor apparatus 200 of the second embodiment. That is, upon contacting the inlet 14, an analyte solution flows into the flow passage defined by the groove 15 under capillary phenomenon, and the flowing analyte solution directly reaches the detection portion 13 so that measurement is conducted.

At this time, as shown in FIG. 30(b), since, of the space left between the periphery of the detection element 3 and the inner wall of the element storage recess 5, a part overlapping with the groove 15 is closed by the auxiliary substrate 44, the auxiliary substrate 44 helps restrain the analyte solution from finding its way into the space. Although, of the space left between the periphery of the detection element 3 and the inner wall of the element storage recess 5, a space located perpendicularly to the groove 15 (the exposed space portion as shown in FIG. 30(a)) is not closed by the auxiliary substrate 44, the auxiliary substrate 44 helps restrain the analyte solution from finding its way into the space. This is because, as shown in FIG. 30(a), a third partition portion 48 lying between the hole portion 45 and the third through hole 46 in the auxiliary substrate 44, and a fourth partition portion 49 lying between the hole portion 45 and the fourth through hole 47 in the auxiliary substrate 44 act to separate the flow passage and the space.

Accordingly, the sensor apparatus 500 is capable of restraining an analyte solution from flowing into an unwanted area, and thus suppressing electrical short-circuiting that is caused between the individual wiring lines. Moreover, since an analyte solution hardly flows into an unwanted area other than the flow passage, it is possible to render the amount of an analyte solution under measurement uniform.

The invention is not limited to the afore-stated embodiments, and may therefore be carried into effect in various forms.

While, in the afore-stated embodiments, the detection portion 13 is illustrated as comprising a metal film and an aptamer immobilized on the surface of the metal film, for example, in a case where a target substance contained in an analyte solution reacts with the metal film, the detection portion 13 may be composed solely of the metal film without using an aptamer. In another alternative, the detection portion 13 may be defined by a region between the first IDT electrode 11 and the second IDT electrode 12 on the surface of the element substrate 10 constructed of a piezoelectric substrate without using a metal film. In this case, an analyte solution is applied directly to the surface of the element substrate 10 to detect the physical properties, such as the viscosity, of the analyte solution. More specifically, a phase change in SAW entailed by, for example, a change of the viscosity of the analyte solution present on the detection portion 13 is read out. Moreover, an aptamer may be immobilized on the surface of a non-conducting film instead of a metal film.

Moreover, while, in the afore-stated embodiments, the detection element 3 is illustrated as being a surface acoustic wave element, the detection element 3 is not limited to this. For example, a detection element 3 in which an optical waveguide or the like is formed so that surface plasmon resonance occurs, may be used. In this case, for example, a change in refractive index of light in the detection portion is read out. In another alternative, a detection element 3 which an oscillator is formed on a piezoelectric substrate such as crystal may be used. In this case, for example, a change in oscillation frequency in the oscillator is read out.

Moreover, as the detection element 3, a plurality of kinds of devices may be provided on the same substrate. For example, an enzyme electrode of an enzyme electrode method may be provided next to the SAW element. In this case, measurement by the enzyme method is possible as well as the immunization method using an antibody or an aptamer, so that items that can be examined at one time can be increased.

Moreover, while, in the afore-stated embodiments, the first cover member 1 is illustrated as comprising the first substrate 1a and the second substrate 1b, and the second cover member 2 is illustrated as comprising the third substrate 2a and the fourth substrate 2b, each cover member is not limited to this, and may therefore comprise substrates formed integrally with each other. For example, a first cover member 1 comprising a first substrate 1a and a second substrate 1b which are combined in one piece may be used.

Moreover, while the afore-stated embodiments employ a single detection element 3, a plurality of detection elements 3 may be provided. In this case, the element storage recess 5 is formed for each detection element 3 on an individual basis, or alternatively the element storage recess 5 is designed to have a length or width large enough to receive all of the detection elements 3.

Moreover, modified examples and forms of the constituent components concerned with one of the embodiments may be applied to the sensor apparatus according to another embodiment without departing from the technical concept of the invention. For example, the modified example of the sensor apparatus 200 of the second embodiment may be applied to the sensor apparatus 300 of the third embodiment.

REFERENCE SIGNS LIST

1: First cover member
1a: First substrate
1b: Second substrate
1A: Intermediate cover member
1Aa: First portion
1Ab: Second portion
2: Second cover member
2a: Third substrate
2b: Fourth substrate
3: Detection element
4: Recess-forming through hole
5: Element storage recess
6: Terminal
7: Wiring line
8: Cutaway
9: Filler member
10: Element substrate
11: First IDT electrode
12: Second IDT electrode
13: Detection portion
14: Inlet
15: Groove (flow passage)
16: First through hole
17: Second through hole
18: Outlet
19: First extraction electrode
19e: End
20: Second extraction electrode
20e: End
21: First protective member
22: Second protective member
23: First vibration space
24: Second vibration space
27: Lead wire (thin metal wire)
28: Insulating member
31: Mounting member
35: Auxiliary substrate

The invention claimed is:

1. A sensor apparatus, comprising:
   a first cover member;
   a detection element comprising
      an element substrate located on an upper surface of the first cover member, and
      a detection portion configured to detect an analyte, the detection portion being located on an upper surface of the element substrate;
   a terminal located on the upper surface of the first cover member and electrically connected to the detection element;
   an intermediate cover member located on the upper surface of the first cover member and having a space with the detection element;
   a filler member located in the space between the detection element and the intermediate cover member;
   a second cover member configured to cover at least a part of the detection element and joined to at least one of the first cover member and the intermediate cover member;
   an inlet into which the analyte flows; and
   a flow passage which is continuous with the inlet, is surrounded by the intermediate cover member and the second cover member, and extends at least to the detection portion.

2. The sensor apparatus according to claim 1,
   wherein the filler member comprises a different material from materials constituting the intermediate cover member and the element substrate.

3. The sensor apparatus according to claim 1,
   wherein the intermediate cover member comprises a first portion and a second portion, and
   in a top view, the detection element is located between the first portion and the second portion.

4. The sensor apparatus according to claim 3,
   wherein the first portion is located closer to the inlet than the second portion, and
   the filler member is located between the detection element and the first portion in the space.

5. The sensor apparatus according to claim 1,
   wherein, in a top view, the detection element is surrounded by the intermediate cover member.

6. The sensor apparatus according to claim 5,
   wherein, in a top view, the filler member surrounds an outer periphery of the detection element.

7. The sensor apparatus according to claim 1,
wherein the detection element comprises an extraction electrode electrically connected to the detection portion,
the extraction electrode and the terminal are connected to each other via a lead wire, and
the filler member covers at least a part of the extraction electrode, at least a part of the lead wire, or at least a part of the terminal.

8. The sensor apparatus according to claim 7,
wherein the filler member covers the at least a part of the extraction electrode, the at least a part of the lead wire, and the at least a part of the terminal.

9. The sensor apparatus according to claim 1, further comprising:
a liquid absorbing member located on the upper surface of the first cover member and lying in a position opposite the inlet with respect to the detection element.

10. The sensor apparatus according to claim 9,
wherein the liquid absorbing member contacts the detection element.

11. The sensor apparatus according to claim 9,
wherein the liquid absorbing member contacts the upper surface of the first cover member and a lower surface of the second cover member.

12. The sensor apparatus according to claim 1,
wherein the first cover member has a flat plate shape, and
a thickness of the intermediate cover member is greater than a thickness of the detection element.

13. The sensor apparatus according to claim 12,
wherein a thickness of the filler member is smaller than the thickness of the intermediate cover member, and the thickness of the filler member is greater than the thickness of the detection element.

14. The sensor apparatus according to claim 1,
wherein the flow passage is surrounded by the first cover member, the intermediate cover member, and the second cover member.

15. The sensor apparatus according to claim 1,
wherein the inlet passes through the second cover member in a thickness direction thereof.

16. The sensor apparatus according to claim 1,
wherein the inlet is located between the first cover member and the second cover member.

* * * * *